United States Patent
Zhang et al.

(10) Patent No.: US 6,387,981 B1
(45) Date of Patent: May 14, 2002

(54) RADIOPAQUE DENTAL MATERIALS WITH NANO-SIZED PARTICLES

(75) Inventors: Xiaodong Zhang, Woodbury; Brant Ulrick Kolb, Afton; Douglas Alan Hanggi, Woodbury; Sumita Basu Mitra, West St. Paul; Paula D'Nell Ario; Richard Paul Rusin, both of Woodbury, all of MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 09/429,185

(22) Filed: Oct. 28, 1999

(51) Int. Cl.⁷ .......................... A61K 6/083; C08K 3/22; C08K 3/36
(52) U.S. Cl. .................. 523/117; 523/116; 522/81; 522/83; 522/92; 522/95; 522/908; 524/430; 524/431; 524/432; 524/433; 524/492; 524/493; 524/780; 524/781; 524/783; 524/784; 524/785; 524/789
(58) Field of Search ........................ 252/478; 522/81, 522/83, 92, 95; 523/115, 116, 117, 118; 524/430, 431, 432, 433, 492, 493, 780, 781, 783, 784, 785, 789

(56) References Cited

U.S. PATENT DOCUMENTS

| | | | |
|---|---|---|---|
| 2,984,628 A | 5/1961 | Alexander et al. | |
| 3,018,262 A | 1/1962 | Schroeder | |
| 3,066,112 A | 11/1962 | Bowen | |

(List continued on next page.)

FOREIGN PATENT DOCUMENTS

| | | |
|---|---|---|
| CA | 2202732 | 10/1997 |
| DE | 195 40 623 A1 | 5/1997 |
| EP | 0 173 567 | 3/1986 |
| EP | 0 184 467 A2 | 6/1986 |
| EP | 0 094 914 | 9/1986 |
| EP | 0 434 334 | 6/1991 |
| EP | 0 530 926 | 3/1993 |
| EP | 0 712 912 A2 | 5/1996 |
| EP | 0 841 304 A1 | 5/1998 |
| GB | 2310855 | 9/1997 |
| JP | 58079818 A | 5/1983 |
| JP | 58135131 A | 8/1983 |
| JP | 3-46407 | 6/1984 |
| JP | 59107969 A | 6/1984 |
| JP | 60103033 A | 6/1985 |
| JP | 60137827 A | 7/1985 |
| JP | 4-72768 | 9/1985 |
| JP | 60176920 A | 9/1985 |
| JP | 60255622 A | 12/1985 |
| JP | 61141620 A | 6/1986 |
| JP | 61227917 A | 10/1986 |
| JP | 61270217 A | 11/1986 |
| JP | 62065932 A | 3/1987 |
| JP | 62091421 A | 4/1987 |
| JP | 62128924 A | 6/1987 |
| JP | 62212224 A | 9/1987 |
| JP | 62226815 A | 10/1987 |
| JP | 63002809 A | 1/1988 |
| JP | 1076919 A | 3/1989 |
| JP | 1079015 A | 3/1989 |
| JP | 1083518 A | 3/1989 |
| JP | 1083519 A | 3/1989 |
| JP | 1083520 A | 3/1989 |
| JP | 1176225 A | 7/1989 |
| JP | 2137729 A | 5/1990 |
| JP | 2137730 A | 5/1990 |
| JP | 2137731 A | 5/1990 |
| JP | 2137732 A | 5/1990 |
| JP | 3174326 A | 7/1991 |
| JP | 4031307 A | 2/1992 |
| JP | 4089319 A | 3/1992 |
| JP | 7118016 A | 5/1995 |
| JP | 8277114 | 10/1996 |
| JP | 9-194674 | 7/1997 |
| JP | 9235119 A | 9/1997 |
| JP | 094674 A | 11/1997 |
| WO | WO 96/34829 | 11/1976 |
| WO | WO 93/05875 | 4/1993 |
| WO | WO 98/13008 | 4/1998 |
| WO | WO 99/17716 | 4/1999 |
| WO | WO 99/65453 | 12/1999 |
| WO | WO 00/20494 | 4/2000 |
| WO | WO00/20494 | 4/2000 |

OTHER PUBLICATIONS

Burgard et al., "Routes to Deagglomerated Nanopower By Chemical Synthesis," *Materials Research Society Symposium Proceedings*, vol. 346, Materials Research Society (1994).

Burgard et al., "Synthesis and Colloidal Processing of Nanocrystalline ($Y_2O_3$–Stabilized) $ZrO_2$ Powders By a Surface Free Energy Controlled Process," *Materials Research Society Symposium Proceedings*, vol. 432, Materials Research Society (1997).

Chatry et al., "The Role of Complexing Ligands in the Formation of Non–Aggregated Nanoparticles of Zirconia," *Journal of Sol–Gel Science and Technology*, vol. 1, pp. 233–240 (1994).

Lewis, Sr., Ed., *Hawley's Condensed Chemical Dictionary*, Thirteenth Ed., John Wiley and Sons, Publ., New York, Title Page, Publication Page, and p. 563 (1997).

Matijevic, Ed., *Surface and Colloid Science*, vol. 6, John Wiley and Sons, Publ., pp. 23–30 (1973).

Watts et al., "Determination of Polymerization Shrinkage Kinetics in Visible–Light–Cured Materials: Methods Development," *Dential Materials*, vol. 7, No. 4, pp. 281–287 (Oct., 1991).

(List continued on next page.)

*Primary Examiner*—Peter Szekely

(57) ABSTRACT

A dental material comprising a hardenable resin, a non-heavy metal oxide particle and a heavy metal oxide. The dental materials can be radiopaque, strong, translucent, or resistant to toothbrush abrasion, or combinations thereof.

58 Claims, 1 Drawing Sheet

U.S. PATENT DOCUMENTS

| | | | |
|---|---|---|---|
| 3,117,099 | A | 1/1964 | Proops et al. |
| 3,442,817 | A | 5/1969 | Luebke et al. |
| 3,514,252 | A | 5/1970 | Levy et al. |
| 3,539,533 | A | 11/1970 | Lee et al. |
| 3,629,187 | A | 12/1971 | Waller |
| 3,708,296 | A | 1/1973 | Schlesinger |
| 3,709,706 | A | 1/1973 | Sowman |
| 3,709,866 | A | 1/1973 | Waller |
| 3,729,313 | A | 4/1973 | Smith |
| 3,741,769 | A | 6/1973 | Smith |
| 3,751,399 | A | 8/1973 | Lee et al. |
| 3,766,132 | A | 10/1973 | Lee et al. |
| 3,808,006 | A | 4/1974 | Smith |
| 3,860,556 | A | 1/1975 | Taylor |
| 4,002,669 | A | 1/1977 | Gross et al. |
| 4,069,055 | A | 1/1978 | Crivello |
| 4,071,424 | A | 1/1978 | Dart et al. |
| 4,115,346 | A | 9/1978 | Gross et al. |
| 4,216,288 | A | 8/1980 | Crivello |
| 4,250,053 | A | 2/1981 | Smith |
| 4,250,311 | A | 2/1981 | Crivello |
| 4,259,117 | A | 3/1981 | Yamauchi et al. |
| 4,292,029 | A | 9/1981 | Craig et al. |
| 4,308,190 | A | 12/1981 | Walkowiak et al. |
| 4,327,014 | A | 4/1982 | Kawahara et al. |
| 4,379,695 | A | 4/1983 | Orlowski et al. |
| 4,387,240 | A | 6/1983 | Berg |
| 4,389,497 | A | 6/1983 | Schmitt et al. |
| 4,394,403 | A | 7/1983 | Smith |
| 4,404,150 | A | 9/1983 | Tsunekawa et al. |
| 4,427,799 | A | 1/1984 | Orlowski et al. |
| 4,503,169 | A | 3/1985 | Randklev |
| 4,544,359 | A | 10/1985 | Waknine |
| 4,545,924 | A | 10/1985 | Ritter, II |
| 4,612,138 | A | 9/1986 | Keiser |
| 4,617,327 | A | 10/1986 | Podszun |
| 4,619,817 | A | 10/1986 | Stambaugh et al. |
| 4,642,126 | A | 2/1987 | Zador et al. |
| 4,649,165 | A | 3/1987 | Kuhlmann |
| 4,652,274 | A | 3/1987 | Boettcher et al. |
| 4,661,540 | A | 4/1987 | Le et al. |
| 4,696,955 | A | 9/1987 | Kuhlmann |
| 4,719,091 | A | 1/1988 | Wusirika |
| 4,737,593 | A | 4/1988 | Ellrich et al. |
| 4,746,685 | A | 5/1988 | Masuhara et al. |
| 4,769,351 | A | 9/1988 | Soumiya et al. |
| 4,772,511 | A | 9/1988 | Wood et al. |
| 4,772,530 | A | 9/1988 | Gottschalk et al. |
| 4,778,671 | A | 10/1988 | Wurisika |
| 4,784,794 | A | 11/1988 | Kato |
| 4,868,288 | A | 9/1989 | Meier |
| 4,874,450 | A | 10/1989 | Gottschalk |
| 4,886,624 | A | 12/1989 | Gradeff et al. |
| 4,923,905 | A | * 5/1990 | Masuhara et al. .......... 523/116 |
| 4,927,560 | A | 5/1990 | Osaka et al. |
| 4,931,414 | A | 6/1990 | Wood et al. |
| 4,946,665 | A | 8/1990 | Recasens et al. |
| 4,954,414 | A | 9/1990 | Adair et al. |
| 4,985,229 | A | 1/1991 | Obitsu et al. |
| 4,985,340 | A | 1/1991 | Palazzotto et al. |
| 5,037,597 | A | 8/1991 | Matchett |
| 5,055,372 | A | 10/1991 | Shanklin et al. |
| 5,057,393 | A | 10/1991 | Shanklin et al. |
| 5,073,476 | A | 12/1991 | Meier et al. |
| 5,084,586 | A | 1/1992 | Farooq |
| 5,089,536 | A | 2/1992 | Palazzotto |
| 5,124,417 | A | 6/1992 | Farooq |
| 5,190,583 | A | 3/1993 | Menzel et al. |
| 5,234,870 | A | 8/1993 | Osaka et al. |
| 5,275,759 | A | 1/1994 | Osaka et al. |
| 5,332,429 | A | 7/1994 | Mitra et al. |
| 5,460,701 | A | 10/1995 | Parker et al. |
| 5,470,910 | A | 11/1995 | Spanhel et al. |
| 5,545,676 | A | 8/1996 | Palazzotto et al. |
| 5,558,849 | A | 9/1996 | Sharp |
| 5,593,781 | A | 1/1997 | Nass et al. |
| 5,609,675 | A | 3/1997 | Noritake et al. ............... 106/35 |
| 5,643,497 | A | 7/1997 | Kaga et al. |
| 5,648,407 | A | 7/1997 | Goetz et al. |
| 5,658,376 | A | 8/1997 | Noguchi et al. |
| 5,698,483 | A | 12/1997 | Ong et al. |
| 5,760,126 | A | 6/1998 | Engle et al. |
| 5,776,239 | A | 7/1998 | Bruno |
| 5,830,242 | A | 11/1998 | Yao |
| 5,856,373 | A | 1/1999 | Kaisaki et al. |
| 5,879,715 | A | 3/1999 | Higgins et al. |
| 5,886,069 | A | 3/1999 | Bolt |
| 5,935,275 | A | 8/1999 | Burgard et al. |
| 5,936,006 | A | 8/1999 | Rheinberger et al. |
| 5,942,559 | A | 8/1999 | Voser et al. ................. 523/115 |
| 6,025,406 | A | 2/2000 | Oxman et al. |
| 6,136,886 | A | 10/2000 | Deguchi |

OTHER PUBLICATIONS

Definition of "binary compound," Oct. 9, 1997, [retrieved on Feb. 16, 2001] Retrieved from the © On–line Medical Dictionary using Internet <URL: http:/www.graylab.ac.uk/cgi–bin/omd?binary+compound>, 1 page.

Definition of "oxide," Oct. 9, 1997, [retrieved on Feb. 16, 2001] Retrieved from the © On–line Medical Dictionary using Internet <URL: http:/www.graylab.ac.uk/cgi–bin/omd?oxide>, 1 page.

*Grant and Hackh's Chemical Dictionary*, 5$^{th}$ Edition, Dr. Roger Grant, Ed., Title Page, Publication Page, p. 106, and p. 231 (1987).

Craig, "Restorative Dental Materials," 8$^{th}$ ed., 1989, p. 256.

C.W. Macosko, "Rheology Principles, Measurements, and Applications," VCH Publishers, Inc., New York, 1994, p. 92.

W.B. Blumenthal, "The Chemical Behavior of Zirconium," D. Van Nostrand Company, Princeton, NJ, pp. 311–338.

"Perthometer, Surface Texture Parameters," Mahr GMB, Gottingen, Germany ed. Sep. 1, 1999, p. 10.

Patent Abstracts of Japan, vol. 1997, No. 11, Nov. 28, 1997; and JP 09/194674 A, Jul. 29, 1997 (abstract).

* cited by examiner

—0.05 μm

RADIOPAQUE DENTAL MATERIALS WITH NANO-SIZED PARTICLES

FIELD OF THE INVENTION

The invention relates broadly to dental materials filled with a non-heavy metal oxide and a heavy metal oxide to provide radiopaque dental materials that can be used as restoratives, adhesives, cements, orthodontic devices, mill blanks and prostheses. More specifically, the invention relates to hardenable dental materials filled with particles of silica and a heavy metal oxide, where the particles impart radiopacity, high strength, and good resistance to abrasion.

BACKGROUND

Dental materials generally have unique requirements as compared to the broad spectrum of composite materials. For health reasons, dental materials should be suitable for use in the oral environment. In certain instances, strength and durability of a dental material is important to ensure satisfactory performance. For example, in dental work that is performed at dentition locations where mastication forces are generally great, high stength and durability is desirable. In other instances, aesthetic character or quality (e.g., luster and translucency) is highly desired. This is often the case where dental work is performed at locations where a tooth repair or restoration can be seen from a relatively short distance.

Strength in a dental material is typically achieved by adding fillers. Generally, a dental material possessing greater mechanical strength characteristics is filled or loaded with larger sized particles; i.e particles having a diameter greater than about 0.4 micrometers. These materials are often referred to as hybrid composites. A disadvantage to these composites, however, is their tendency to lack luster and aesthetic character. Another disadvantage of composites with large-sized particles is that with repeated toothbrushing (a requirement for oral hygiene), the hardened resin can wear away, exposing the large filler particles and leave a dull, unaesthetic surface. This can subsequently lead to plaque accumulation.

Increasing filler levels can also increase the strength of a dental material. However, this can lead to increased visual opacity, thereby reducing translucency and aesthetic quality.

Canadian Patent Application 2,202,732 teaches polymerizable dental materials comprising a sol of surface modified silica particles in a liquid, organic dispersion agent. The silica particles comprise about 35 wt % of the dental material.

Good rheological properties in unhardened dental materials are advantageous to a dental practitioner. This allows the practitioner to easily manipulate and place the material in its desired location and achieve proper contact and anatomical form before hardening or curing. Nanometer sized ("nano-sized") silica particles, most often in the form of fumed silica, have been dispersed in polymerizable dental resins. A fumed silica material available from DeGussa, under the trade designation OX-50, has had widespread use. Materials made with fumed silica dispersed at high loading levels within the resins, however, result in dilatant compositions that are generally impractical for dental practice. A well-recognized dental reference book by Craig, entitled, "Restorative Dental Materials," 8th ed., 1989 teaches that highly-loaded fumed silica materials generally provide materials with poor rheological properties. (See e.g., p.256 of Craig.) Thus, conventional materials whose concentrations of an inorganic component (particles) are adjusted for a desired strength, typically result in undesirably dilatant materials.

It has also been the practice to incorporate pre-polymerized particles to overcome the dilatant rheology. These, however, can result in low strength materials.

It is generally desired that the dental material blends well with the surrounding dentition and looks life-like. Aesthetic quality in dental materials is typically achieved by creating material that has tooth-like colors/shades. "Microfills," a certain class of dental materials, tend to have some luster, to better replicate tooth appearance. One example of a "microfill" is commercially available under the trade designation SILUX PLUS (3M Co., St. Paul, Minn.). Microfills, however, generally have less mechanical strength than hybrid composites or "macrofills." Thus, in current practice, for applications where high strength and high aesthetic quality are desired, a practitioner is typically required to first use an underlying foundation of a material possessing high physical strength followed by an overlying layer of a microfill.

Radiopacity of a dental material can be useful in dentistry. Radiopaque materials can be examined using standard dental X-ray equipment, thereby facilitating long term detection of marginal leakage or caries in tooth tissues adjacent to a hardened material. U.S. Pat. No. 4,503,169 describes a radiopaque, low visual opacity (i.e. translucent) dental composite with non-vitreous zirconia-silica microparticles made by a sol-gel process.

SUMMARY OF THE INVENTION

The invention provides dental material comprising a hardenable resin, non-heavy metal oxide particles, and a heavy metal oxide. The dental materials have high aesthetic quality, high strength, and good resistance to abrasion.

"Hardenable" is descriptive of a material that can be cured or solidified e.g., by heating to remove solvent, heating to cause polymerization, chemical crosslinking, radiation-induced polymerization or crosslinking, or the like.

"Non-heavy metal oxide" means any oxide of elements other than those of heavy metals.

"Heavy metal oxide" means an oxide of metals having an atomic number greater than 28.

In an aspect of the invention, silica particles combined with a heavy metal oxide can provide a strong, radiopaque yet translucent (i.e. low visual opacity) dental material.

In another aspect of the invention, the dental materials of the invention can be used as dental adhesives, artificial crowns, anterior or posterior fillings, casting materials, cavity liners, cements, coating compositions, mill blanks, orthodontic devices, restoratives, prostheses, and sealants.

In a further aspect of the invention, the hardenable resin can be an acrylate, methacrylate, or epoxy or combinations thereof.

In another aspect of the invention, methods of using the materials of the invention comprise placing the material in the oral environment, where the surface or topography is changed prior to or after the placement in the mouth and hardening the material.

DETAILED DESCRIPTION OF THE PREFERRED EMBODIMENTS

Figure 1:
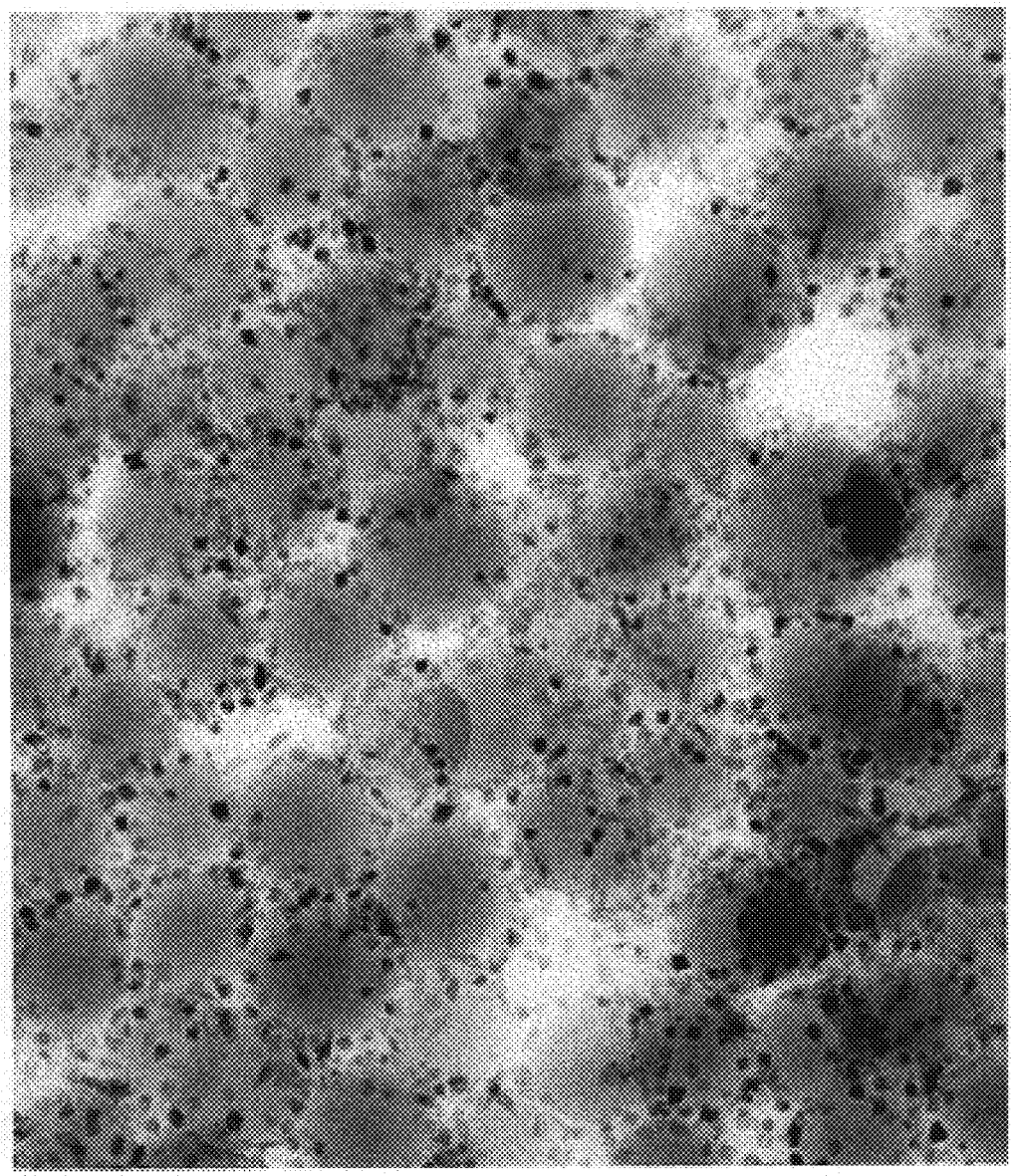
FIG. 1 is a digital image of a TEM (transmission electron micrograph) of a preferred embodiment of a dental material of the invention, taken at 300,000× magnification.

The present invention provides a material that possesses high strength, high aesthetic quality and radiopacity. High aesthetic quality is achieved by providing a dental material that possesses high translucency and good polish. Advantageously, the dental materials of the invention are also preferably able to retain their polish even after exposure to repetitive abrasion. The dental materials of the invention comprise a hardenable resin having at least two components: a non-heavy metal oxide and a heavy metal oxide. The particles are stable when dispersed in the hardenable resin, and preferably remain stable even after hardening.

The dental materials of the present invention can be used for example, as dental adhesives, artificial crowns, anterior or posterior fillings, casting materials, cavity liners, cements, coating compositions, mill blanks, orthodontic devices, restoratives, prostheses, and sealants. In a preferred aspect, the dental material is a dental restorative. The restoratives of the invention can be placed directly in the mouth and cured (hardened) in situ, or alternatively, may be fabricated into a prosthesis outside the mouth and subsequently adhered in place inside the mouth.

Dental materials of the present invention can be chemically curable or light curable compositions. Light curable materials should have an appropriate initiator system. Chemically curable materials can be auto-cured (e.g. via redox initiators). Alternatively, the materials of the invention can be hardened by a combination of auto- and light-cure.

It has been found that loading a dental material with nano-sized particles of a non-heavy metal oxide and a heavy metal oxide imparts a combination of radiopacity, high strength, and high translucency. Dental materials containing specified amounts of nano-sized inorganic oxide particles of the present invention have especially desirable handling (rheological) properties in an unhardened state and exceptionally high strength in a hardened state.

Strength can be characterized by mechanical measurements such as compressive strength and diametral tensile strength. High compressive strength in a dental material is advantageous due to the forces exerted by mastication on dental repairs, replacements and restorations. Diametral tensile strength indicates the dental material's ability to withstand compression forces that introduce a tensile stress in the material. Tests for each strength measurement are set out below in the Test Methods.

The dental materials of the invention preferably have a compressive strength of at least about 35 MPa; more preferably, the materials have a compressive strength of at least about 200 MPa; most preferably, the materials have a compressive strength of at least about 350 MPa.

Hardened dental materials of the invention preferably have a diametral tensile strength of at least about 15 MPa; more preferably at least about 40 MPa; most preferably at least about 60 MPa.

Aesthetic quality of a dental material, although a somewhat subjective characteristic (yet well-understood in the dental industry), can be preferably quantified in one aspect by a visual opacity measurement. Visual opacity is indicative of dental material's level of translucency—low visual opacity is desired so that the hardened dental material will have a life-like luster. To achieve good translucency, it is desirable to minimize the scattering of light as it passes through a material. Generally, this has been accomplished by selecting particles in which the maximum diameter is less than the wavelength of the transmitted light, where visible light is about 5,500 angstroms (550 nm). The dental materials of the present invention preferably have a visual opacity of about 0.05 to 0.5; more preferably about 0.05 to 0.35; most preferably about 0.05 to 0.25.

Polishability of a dental material also contributes to the aesthetic character and quality of the material. The ability of a dental material to have a glossy finsh and life-like luster upon polishing is highly desirable. An even greater benefit is the ability of a hardened material to retain its luster even after repetitive abrasive contact, such as tooth brushing. It has been surprisingly found that materials of the present invention, when made in the preferred embodiment of a dental restorative, have high polishability and are able to retain the polish and luster after repetitive tooth brushing.

To evaluate a hardened, polished dental material's ability to retain its polish, a surface roughness measurement can preferably be determined by subjecting the material to a Toothbrush Abrasion Resistance Test. Using a surface roughness analyzer, commonly referred to as a surface profilometer, the material's roughness (or smoothness) after the Toothbrush Abrasion Resistance Test can be measured. A preferred apparatus to obtain the surface roughness is the WYKO RST PLUS Surface Profiling System (WYKO Corporation, Tuscon, Ariz.), using the test procedure described below in the Test Methods. The surface roughness measurement provides the average variation within the surface by measuring the average height of the profile above and below a central line. After subjecting the dental materials of the invention to the Toothbrush Abrasion Resistance Test, the dental materials preferably have a surface roughness of less than about 0.2 $\mu$m; more preferably less than about 0.15 $\mu$m.

Materials of the invention preferably possess good rheological properties. These properties as well as strength can be enhanced by using surface-modifying agents to treat the surface of the particles. Surface treatment (surface-modification) enhances the dispersibility of the particles and their ability to bind into the matrix.

Practitioners generally desire good handling properties in a dental material, as it often translates to time savings. For example, in dental restorative work, it is desirable that dental materials do not slump because after a practitioner places the material in the mouth and manipulates the material by contouring and feathering, the practitioner generally wants the imparted shape to remain unchanged until the material is hardened. Materials used for restorative work, having a sufficiently high yield stress generally will not slump; that is, they will not flow under the stress of gravity. The yield stress of a material is the minimum stress required to cause the material to flow, and is described in "Rheology Principles, Measurements, and Applications" by C. W. Macosko, VCH Publishers, Inc., New York, 1994, p. 92. If the stress due to gravity is below the yield stress of the material, then the material will not flow. The stress due to gravity, however, will depend on the mass of dental material being placed as well as the shape.

"Contouring" refers to the process of shaping a material (using dental instruments) so that it resembles the natural dental anatomy. For easy contouring, materials should have a sufficiently high viscosity that they maintain their shape after manipulation with a dental instrument, and yet the viscosity should not be so high that it is difficult to shape the material. "Feathering" refers to the process of reducing the dental material to a thin film in order to blend the material into the natural dentition. This is done with a dental instrument at the margin of the manipulated material and the natural dentition. It is also desirable that the dental material not stick to placement instruments, to minimize further alteration of the shape or surface topography.

In a preferred embodiment where the dental material of the invention is a restorative, the dental material preferably has little to no slump, yet easily adapts to, for example, a cavity preparation, and is easily contoured and feathered. Preferably, the dental materials of the invention do not stick to placement instruments, and are advantageously, overall, fast and easy to use in dental procedures such as, for example, restoring tooth structure.

Surprisingly, it has been found that the dental materials of the invention can possess improved and desirable shear thinning behavior. That is, they can have a low viscosity when subjected to high stress, and high viscosity when subjected to low stress. The low viscosity under high stress allows a practitioner to feather the material over a tooth surface and carve the dental material. Advantageously, the high viscosity under low stress allows the material to maintain its shape (i.e. no slumping) after a practitioner manipulates the material to match the contour of the tooth.

Suitable non-heavy metal oxide particles that can be used in the dental materials of the invention include, for example, silica, titanium oxide, aluminum oxide, and the like. Preferably, the non-metallic oxide particles are silica that are present in the dental material in various forms, including for example, fumed silica, colloidal silica, or aggregated silica particles. As used herein, "colloidal" means discrete (individual) and unassociated (i.e. non-aggregated and non-agglomerated). "Agglomerated" as used herein, is descriptive of a weak association of particles usually held together by charge or polarity and can be broken down into smaller entities. "Aggregated," as used herein, is descriptive of a strong association of particles often bound together by, for example, residual chemicals treatment; further breakdown of the aggregates into smaller entities is very difficult to achieve.

The dental materials of the invention preferably comprise silica particles that have an average diameter of less than about 300 nanometers (nm). More preferably, the primary (individual) silica particles have an average diameter of less than about 200 nm, and most preferably, the average diameter is less than about 100 nm. The silica particles may be aggregated, where the aggregate comprises a plurality of smaller sized silica particles; however, it is still desirable and preferable that the total aggregate size be less than about 300 nm, more preferably less than about 200 nm, most preferably less than about 100 nm. These measurements are preferably based on a TEM (transmission electron microscopy) method, whereby a population of particles such as what is show in FIG. 1, is analyzed to obtain an average particle diameter. A preferred method for measuring the particle diameter is set out below, in the Test Methods. Referring now to FIG. 1, a preferred embodiment of the invention where a material having silica particles and zirconium oxide particles in a resin is provided.

The silica used in the dental materials of the present invention are preferably substantially spherical and substantially non-porous. Although the silica is essentially pure, it may contain small amounts of stabilizing ion such as ammonium and alkaline metal ions.

Preferred silicas for use in the materials of the invention are commercially available from Nalco Chemical Co. (Naperville, Ill.) under the product designation NALCO COLLOIDAL SILICAS. For example, preferred silicas include NALCO products 1040, 1042, 1050, 1060, 2327 and 2329. Suitable fumed silicas include for example, products sold under the tradename AEROSIL series OX-50, -130, -150, and -200 available from DeGussa AG, (Hanau Germany), and CAB-O-SIL M5 available from Cabot Corp. (Tuscola, Ill.).

Surface-treating the nano-sized silica particles before loading into the dental material can provide a stable dispersion in the resin. "Stable", as used herein, means a dental material in which the particles do not agglomerate after standing for a period of time, such as about 24 hours, under standard ambient conditions—e.g. room temperature (about 20–22° C.), atmospheric pressure, and no extreme electromagnetic forces. Preferably, the surface-treatment stabilizates the silica particles so that the particles will be well dispersed in the polymerizable resin and results in a substantially homogeneous composition. Furthermore, it is preferred that the silica be modified over at least a portion of its surface with a surface treatment agent so that the stabilized particle can copolymerize or react with the polymerizable resin during curing.

The silica particles of the present invention are preferably treated with a resin-compatibilizing surface treatment agent. Particularly preferred surface treatment or surface modifying agents include silane treatment agents capable of polymerizing with a resin. Preferred silane treatment agent include γ-methacryloxylpropyltrimethoxysilane, available commercially under the trade designation A-174, available commercially from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably a 3-membered ring containing oxygen such as an epoxide.

The heavy metal oxide should be present in an amount effective to impart radiopacity. As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied or customized, depending upon, for example, the particular application and/or the desired radiopacity a practitioner needs to evaluate an X-ray film.

Oxides of heavy metals having an atomic number greater than about 28 are preferred. The heavy metal oxide should be chosen such that undesirable colors or shading are not imparted to the hardened resin in which it is dispersed. For example, iron and cobalt would not be favored, as they impart dark and contrasting colors to the neutral tooth color of the dental material. More preferably, the heavy metal oxide is an oxide of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Most preferably, the oxides of heavy metals having an atomic number greater than 30, but less than 72. Particularly preferred radiopacifying metal oxides include lanthanum oxide, zinc oxide, tin oxide, zirconium oxide, yttrium oxide, ytterbium oxide, barium oxide, strontium oxide, cerium oxide, and combinations thereof. Preferably, the heavy metal oxide component is provided as a sol or particles.

It has been found that incorporation of an effective amount of nano-sized heavy metal oxide particles into dental materials of the invention can yield optically translucent materials with high X-ray opacity and high refractive index. The heavy metal oxide particles preferably have an average diameter of less than about 100 nm. More preferably, the particles are less than about 70 nm, more preferably less than about 60 nm. The heavy metal oxide particles may be aggregated. If so, it is preferred that the aggregated particles are less than about 200 nm, and more preferably are less than about 90 nm.

Preferred sources of unassociated heavy metal oxide particles are sols having particles dispersed in a solution. A zirconia sol, as disclosed in U.S. Pat. No. 5,037,579 (Matchett), is a suitable and preferable heavy metal oxide for use with the dental materials of the invention.

Another preferred zirconia sol is disclosed in U.S. patent application Ser. No. 09/428,374, filed on Oct. 28, 1999, which is incorporated herein. Zirconia sols of U.S. patent application Ser. No. 09/428,374, filed on Oct. 28, 1999, comprise a plurality of single crystal zirconia particles having an average primary particle size of about 20 nm or less, more preferably, having an average primary particle size ranging from about 7–20 nm. As used herein, the term "primary particle size" refers to the size of a non-associated single crystal zirconia particle. Primary particle size is determined by the test method entitled, Crystallite Particle Size and Crystal Form Content, a procedure which resides in the Test Methods section below.

As disclosed in U.S. patent application Ser. No. 09/428, 374, filed on Oct. 28, 1999, the zirconia sols comprise zirconia particles which are highly crystalline in nature. This is important in that crystalline zirconia has a higher refractive index and higher x-ray scattering capability than amorphous zirconia. Crystallinity of zirconia particles may be quantified, for example, using a crystallinity index. Crystallinity index is calculated by dividing the x-ray scattering intensity of the sample material by the x-ray scattering intensity of a known crystalline standard material, for example, calcium stabilized zirconium oxide. A specific test procedure for determining the crystallinity index of zirconia particles is entitled Crystallinity Index Procedure, a description of which resides in the test Methods section below. In the zirconia sols, the zirconia particles have a crystallinity index of about 0.65 or greater. More preferably, the zirconia particles having a crystallinity index of about 0.75 or greater, most preferably about 0.85 or greater.

Of the crystalline portion of the zirconia particles, the predominate crystal lattice forms are cubic and tetragonal with a minor amount of monoclinic phase also being present. Due to the difficulty in separately quantifying cubic and tetragonal crystal lattice structures using x-ray diffraction, the two have been combined and are reported herein as combined cubic and tetragonal. Specifically, the zirconia particles comprise about 70% or greater combined cubic and tetragonal crystal lattice structure. More preferably, the zirconia particles comprise about 75% or greater combined cubic and tetragonal crystal lattice structure, and most preferably comprise about 85% or greater combined cubic and tetragonal crystal lattice structure. In each instance, the balance of the crystalline phase is in the monoclinic crystal lattice structure.

Due to their very small size, the zirconia particles exist in predominately cubic and tetragonal crystal lattice phases without need for an effective amount of a crystal phase stabilizer. As used herein the term "crystal phase stabilizer" refers to a material which may be added to stabilize zirconia in the cubic and/or tetragonal crystal lattice structure. Specifically, crystal phase stabilizers function to suppress transformation from the cubic and/or tetragonal phase to the monoclinic phase. Crystal phase stabilizers include, for example, alkaline-earth oxides such as MgO and CaO, rare earth oxides (i.e., lanthanides) and $Y_2O_3$. "An effective amount" refers to the amount of crystal phase stabilizer necessary to suppress transformation of zirconia from the cubic and/or tetragonal phase to the monoclinic phase. In a preferred embodiment, the zirconia particles comprise less than about 1 wt. % of a crystal phase stabilizer, more preferably less than about 0.1 wt. % of a crystal phase stabilizer.

In zirconia sols of U.S. patent application Ser. No. 09/428, 374 filed on Oct. 28, 1999, the primary particles of zirconia exist in a substantially non-associated (i.e., non-aggregated and non-agglomerated) form. A quantitative measure of the degree of association between the primary particles in the sol is the dispersion index. As used herein the "dispersion index" is defined as the hydrodynamic particle size divided by the primary particle size. The primary particle size is determined using x-ray diffraction techniques as described in the test procedure Crystallite Particle Size and Crystal Form Content" set out below. Hydrodynamic particle size refers to the weight average particle size of the zirconia particles in the aqueous phase as measured by Photon Correlation Spectroscopy (PCS), a description of which resides in the Test Methods section below. If the primary particles are associated, PCS provides a measure of the size of the aggregates and/or agglomerates of primary particles in the zirconia sol. If the particles are non-associated, PCS provides a measure of the size of the primary particles. Accordingly, as the association between primary particles in the sol decreases the dispersion index approaches a value of 1. In the zirconia sols, the primary zirconia particles exist in a substantially non-associated form resulting in a zirconia sol having a dispersion index ranging from about 1–3, more preferably ranging from about 1–2.5, and most preferably ranging from about 1–2.

As further taught in U.S. patent application Ser. No. 09/428,374, filed on Oct. 28, 1999, suitable starting materials for preparing polyether acid zirconium salts include basic zirconium salts such as zirconium carboxylates and basic zirconium salts having counterions that may be displaced with carboxylic acids. Representative examples of basic zirconium salts having counterions that may be displaced with carboxylic acids include zirconium oxynitrate, zirconium oxychloride and zirconium carbonates. Basic zirconium salts are salts of zirconium wherein at least a portion of the cationic charge on the zirconium is compensated by hydroxide or an $O^{2-}$ anion. Because it is difficult in practice to determine whether the oxygen content in basic zirconium salts arises from bound hydroxide or $O^{2-}$, it is common to represent this oxygen content as simply oxygen. Thus, formula (1) set forth below is presented with bound water excluded for simplicity and represents a general formula for zirconium compounds that may be suitable as starting materials for preparing polyether acid zirconium salts.

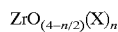

$$ZrO_{(4-n/2)}(X)_n \tag{1}$$

where:

X is a carboxylic acid displaceable counterion; and n ranges from 0.5 to 4.

Representative examples of carboxylic acid displaceable counterions include carboxylates such as acetates, formates and propionates and other counterions such as nitrate, chloride, carbonate or a combination thereof. Zirconium alkoxides, although not formally zirconium salts, may be used as starting materials in the formation of the polyether acid zirconium after initial reaction with a suitable acid to form a basic zirconium salt.

A preferred starting material is an aqueous solution or sol of basic zirconium acetate having the general formula $ZrO_{(4-n/2)}(CH_3COO)_n$, where n ranges from about 1–2. In aqueous solutions, zirconium acetate probably exists as complex polynuclear zirconium cation. Processes for making zirconium acetate are well known in the art (see, for example, W. B. Blumenthal, "The Chemical Behavior of Zirconium", D. Van Nostrand Company, Princeton, N.J., pp. 311–338). Suitable zirconium acetate solutions comprise from about 5–40 wt. % as $ZrO_2$ and range from about 5–40 wt. % acetate. A preferred zirconium acetate sol starting material comprises $ZrO_{1.25}(C_2H_3O_2)_{1.5}$ at 20 wt. % $ZrO_2$ and is commercially available under the trade designation "Nyacol $ZrO_2$(Ac)" from Nyacol Products Corp., Ashland, Mass.

In a preferred process of U.S. patent application Ser. No. 09/428,374, filed on Oct. 28, 1999, a polyether acid zirconium salt is prepared by reacting, in an aqueous solution, a zirconium salt with a polyether carboxylic acid. As presently understood, the polyether carboxylic acid is believed to function to prevent association (i.e., agglomeration and/or aggregation) of the zirconia particles as they are formed during the hydrolysis reaction. In this way, the zirconia particles produced according to the process are substantially non-associated.

Polyether carboxylic acids suitable for use as modifiers in U.S. patent application Ser. No. 09/428,374, filed on Oct. 28, 1999, are water soluble monocarboxylic acids (i.e., containing one carboxylic acid group per molecule) having a polyether tail. The polyether tail comprises repeating difunctional alkoxy radicals having the general formula —O—R—. Preferred R groups have the general formula —$C_nH_{2n}$— and include, for example, methylene, ethylene and propylene (including n-propylene and i-propylene) or a combination thereof. Combinations of R groups may be provided, for example, as random, or block type copolymers.

A preferred class of monovalent polyether radicals may be represented generally by formula (3):

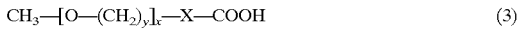
$$CH_3—[O—(CH_2)_y]_x—X—COOH \quad (3)$$

where:

X is a divalent organic linking group;

x ranges from about 1–10; and y ranges from about 1–4.

Representative examples of X include —$X_2$—$(CH_2)_n$— where $X_2$ is —O——S—, —C(O)O—, —C(O)NH— and wherein n ranges from about 1–3.

Examples of preferred polyether carboxylic acids include 2-[2-(2-methoxyethoxy)ethoxy] acetic acid having the chemical structure $CH_3O(CH_2CH_2O)_2CH_2COOH$ (hereafter MEEAA) and 2-(2-methoxyethoxy) acetic acid having the chemical structure $CH_3OCH_2CH_2OCH_2COOH$ (hereafter MEAA). MEAA and MEEAA are commercially from Aldrich Chemical Co., Milwaukee, Wis. as catalog numbers 40,701-1 and 40,700-3, respectively. It is also within the scope of this invention to utilize a mixture of more than one polyether carboxylic acid.

Reaction of the polyether carboxylic acid with a zirconium salt following reaction sequence (1):

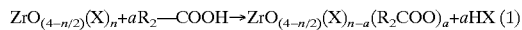
$$ZrO_{(4-n/2)}(X)_n + aR_2—COOH \rightarrow ZrO_{(4-n/2)}(X)_{n-a}(R_2COO)_a + aHX \quad (1)$$

results in the formation of a polyether acid zirconium salt having the general formula $ZrO_{(4-n/2)}(X)_{n-a}(R_2COO)_a$ and liberates (i.e., releases) approximately a stochiometric amount of an acid having the general formula HX. By way of example, when the zirconium salt comprises zirconium acetate ($ZrO_{(4-n/2)}(C_2H_3O_2)_n$) a near stochiometric amount of acetic acid ($C_2H_3O_2H$) is released as a result of the formation of the polyether acid zirconium salt (see, reaction sequence 1a).

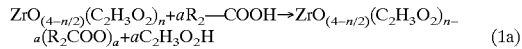
$$ZrO_{(4-n/2)}(C_2H_3O_2)_n + aR_2—COOH \rightarrow ZrO_{(4-n/2)}(C_2H_3O_2)_{n-a}(R_2COO)_a + aC_2H_3O_2H \quad (1a)$$

Salts of zirconium with carboxylic acids are not dissociated in the aqueous phase as the acid is bound to the zirconium atom. The carboxylic acid effects the water solubility of the salt. Attachment of hydrophobic acids (e.g., alkyl acids) to the zirconium causes the salts to be insoluble in water. In fact, even the addition of small acids such as propionic acid and acrylic acid cause the salt to be insoluble in water. In contrast, the polyether acids used in U.S. patent application Ser. No. 09/428,374, filed on Oct. 28, 1999, allow higher molecular weight acids to be used while maintaining the water solubility of the polyether acid zirconium salt. This in turn allows hydrothermal treatment of the dissolved polyether acid zirconium salt in the aqueous phase.

Typically, relative to the zirconium salt starting material, the polyether carboxylic acid is added in an amount ranging from about 2.5–5.0 millimoles per gram equivalent of $ZrO_2$ in the zirconium salt. For the preferred zirconium acetate starting material (i.e., Nyacol $ZrO_2$(Ac)), this range results in the displacement of about 20–50% of the acetate groups. Preferably, the amount of polyether carboxylic acid added should be limited to the minimum amount necessary to prevent association of the resulting zirconia particles. In this way, the amount of acid released during formation of the polyether acid zirconium salt is kept to a minimum. The amount of polyether carboxylic acid added may depend upon such factors as, for example, the molecular weight of the polyether carboxylic acid, the concentration, time and temperature during the hydrolysis reaction.

In further teachings of U.S. patent application Ser. No. 09/428,374, filed on Oct. 28, 1999, typically, the polyether carboxylic acid is added to an aqueous solution of the zirconium salt and the resulting solution is stirred at room temperature for about 30–60 minutes. The polyether carboxylic acid molecules react with the zirconium salt displacing and substituting for at least a portion of the acid groups bound to the zirconium salt. The displaced acid groups are released into the solution as free acid. It will ordinarily be preferred to remove at least a portion of the acid, more preferably substantially all of the acid released during the formation of the polyether acid zirconium salt. It should be noted that removal of the acid may function to shift the reaction equilibrium towards formation of the polyether acid zirconium salt. Suitable techniques for removing the excess acid are known in the art and include, for example, drying or distillation. When the liberated acid has a low boiling point (e.g., <about 175° C.), it may be removed by heating the solution until the aqueous phase evaporates leaving a residue of the polyether acid zirconium salt. The polyether acid zirconium salt must then be dissolved in water prior to hydrolysis.

After formation of the polyether acid zirconium salt and, preferably, removal of the liberated acid, the next step is to hydrolyze an aqueous solution of the polyether acid zirconium salt under conditions sufficient to convert the polyether acid zirconium salt into crystalline zirconia particles. By way of example, when the polyether acid zirconium salt is derived from the acetate salt (see, reaction sequence 1a), the hydrolysis step follows general reaction sequence (2a):

$$ZrO_{(4-n/2)}(C_2H_3O_2)_{n-a}(R_2COO)_a \rightarrow \text{acid modified } ZrO_2 + (n-a)C_2H_3O_2H + aR_2COOH \qquad (2a)$$

The hydrolysis reaction forms acid modified zirconia particles and also produces free carboxylic acids (i.e., $C_2H_3O_2H$ and $R_2COOH$) as a by product. Therefore, the resultant zirconia sol comprises the acid modified zirconia particles and a mixture of two carboxylic acids in water. By acid modified zirconia particles it is meant that at least a fraction of the acids are adsorbed to the surface of the zirconia particles.

The hydrolysis reaction of the polyether acid zirconium salt solution may take place in any suitable reaction vessel. Since the reaction is typically performed under high temperatures and pressures, an autoclave will generally be the preferred type of reaction vessel. One example of a preferred reaction vessel is commercially available as Pressure Reactor Series #4520" from Parr Instruments Co., Moline, Ill.

In operation of the process of U.S. patent application Ser. No. 09/428,374, filed on Oct. 28, 1999, an aqueous solution of the polyether acid zirconium salt is first charged into a reaction vessel. The concentration of the polyether acid zirconium salt solution is typically in the range of 0.5–3 wt. % $ZrO_2$, preferably in the range of 1–2 wt. % $ZrO_2$. However, the concentration may be varied through a wider range depending upon the other reaction conditions. The polyether acid zirconium salt solution is then heated to a temperature sufficient to convert it into zirconia particles. Preferred hydrolysis temperatures range from about 140–250° C., more preferably ranging from about 150–200° C. Typically the reaction vessel is heated to the desired hydrolysis temperature over a period of several hours. Among other considerations, a suitable hydrolysis temperature or temperature range, may be selected in order to minimize degradation and/or decomposition of the polyether carboxylic acid. The pressure maintained in the reaction vessel may be the autogenous pressure (i.e., the vapor pressure of water at the temperature of the reaction) or, preferably, the reaction vessel may be pressured, for example, with an inert gas such as nitrogen. Preferred pressures range from about 1–30 bars. Pressurization of the reaction vessel is believed to reduce or eliminate refluxing of the polyether acid zirconium salt solution within the reaction vessel which may deleteriously affect the properties of the resulting zirconia sol. The time of hydrolysis is typically a function of the hydrolysis temperature and the concentration of the salt solution. Heat is typically applied until the hydrolysis reaction is substantially complete. Generally, the time involved is in the range of about 16–24 hours at a temperature of about 175° C., however, longer or shorter times may also be suitable. The reaction may be monitored by examining the resulting zirconia particles using x-ray diffraction or by examining the amount of free acid in the water phase using IR spectroscopy or HPLC. Upon completion of the hydrolysis, the pressure vessel is allowed to cool and the resulting zirconia sol is removed from the reaction vessel. Although the procedure described above is a batch-wise process, it is also within the scope of this invention to conduct the hydrolysis in a continuous process.

Zirconia sols of U.S. patent application Ser. No. 09/428, 374, filed on Oct. 28, 1999, may be concentrated by removing at least a portion of the liquid phase using techniques well known in the art, for example, evaporation or ultrafiltration. In a preferred method the zirconia sols are concentrated to about 10–40 wt. % $ZrO_2$ using a rotary evaporator.

Zirconia sols prepared in accordance with the method of U.S. patent application Ser. No. 09/428,374, filed on Oct. 28, 1999, typically contain an excess of acid over that normally desired (see, reaction sequence 2a). When it is desired to combine a zirconia sol with an organic matrix material, for example, an organic monomer, it will ordinarily be necessary to remove at least a portion of, more preferably substantially all of, the free acid present in the sol. Typically, the acid may be removed by such conventional methods as drying, dialysis, precipitation, ion exchange, distillation or diafiltration.

Due to the formation of free acid during the hydrolysis reaction, the pH of the as prepared zirconia sols typically ranges from about 1.8–2.2. Dialysis may be used to increase the pH of the sols. Dialyzed sols typically have a pH ranging about 1–4.5, or greater, depending upon the extent of the dialysis. The pH of the sols may also be adjusted by the addition of acids (e.g., concentrated HCl and glacial acetic) and/or base (e.g., aqueous ammonia). Addition of aqueous ammonia has resulted in clear sol to at least pH 6–7.

Dialysis, ion exchange and diafiltration methods may be used to remove the free acid without substantially changing the ratio of the acids adsorbed to the surface of the zirconia particles. Alternatively, removal of excess acid and concentration of the sol may be achieved by first evaporating the water and free acid from the sol to obtain a dry powder. The dry powder may then be redispersed in a desired amount of water to obtain a concentrated sol substantially free of excess acid. It should be noted, however, that this technique may change the ratio of the acids adsorbed to the surface of the zirconia particles in such a way that the ratio of the higher boiling acid to the lower boiling acid is increased.

Optionally, after formation of the zirconia sol, the polyether carboxylic acid groups may be removed or displaced from the zirconia particles of the sol. Removal of the polyether carboxylic acid groups may be advantageous, for example, when the polyether groups would be incompatible with an organic matrix material to which it is desired to add the zirconium sol. Displacement of the polyether carboxylic acid groups may be accomplished, for example, by displacing the polyether acid from the zirconia particles with a carboxylic acid, for example, acetic acid. The carboxylic acid displaces and substitutes for the polyether carboxylic acid groups on the zirconia particles. After displacement, the free polyether carboxylic acid may be removed from the sol using techniques known in the art, for example, dialysis or diafiltration.

Surface treatment of the heavy metal oxide particle promotes the provision of stabilized heavy metal oxide particles. Stabilization allows the heavy metal oxide particles to be well dispersed within the hardenable resin, so as to provide the desired translucency and yet provide the desired mechanical properties (e.g. strength) and radiopacity. A surface treatment agent is preferably chosen to contain functional groups that provide dispersibility and/or reactivity of the surface modified heavy metal oxide particle with(in) the desired hardenable resin. Preferably, the metal oxide particles are treated with an acidic compound. Suitable surface-treatment acids include for example, carboxylic acids, phosphonic acids, and sulfonic acids. More preferably, the surface stabilization is performed with a mixture of acidic compounds. Alternatively, a mixture of acidic compounds where one or more has a polymerizable functionality, can preferably be used. Most preferably, the acidic function is derived from oxyacids of boron, carbon, phosphorus, and sulfur. For example, it has been found that carboxylic acids adsorb particularly well to the surface of zirconia and ceria particles.

A mixture of acids is preferably used to surface treat (modify) the heavy metal oxide particles. Preferably, the acids include the structure R—COOH, where R is an organic radical containing ethylenic unsaturation. R may be branched or straight chained and may be substituted (e.g., by a heteroatom). R typically contains from about 1 to 50 carbon atoms, preferably about 2 to 20 carbon atoms. A particularly preferred group of such acids includes includes R groups with terminal ethylenic unsaturation.

Adsorption of a combination of acids to the particle surface provides a desirable surface modification to impart strength, dispersibility and stability. In a preferred method, colloidal zirconia particles are dispersed in water with acetic acid adsorbed to the surface. The surface modification involves replacement of adsorbed acetic acid with a combination of acids chosen to provide good dispersion and high strength to the final material.

Hydrophilic, non-reactive acids suitable for the surface treatment (modification) include 2-[2-(2-methoxy)ethoxy] ethoxy acetic acid (MEEAA), mono(polyethyleneglycol) succinate, mono(polyethyleneglycol)maleate. These acids provide good dispersion of the particles in the hardenable dental materials of the invention.

Strength is greatly enhanced via copolymerization of surface modifying groups with the hardenable resin. Preferably, this is accomplished by using a reactive surface modifier. Examples of hydrophilic and reactive acids suitable for the surface treament include 2-hydroxymethyl-2-[(N-methacryloxyethyl) carbamoylmethyl]propionic acid (PAMA), mono(acryloxypolyethyleneglycol)succinate, and mono(acryloxypolyethyleneglycol)maleate. Other suitable reactive acids include 2,2-bis[(N-methacryloxyethyl) carbamoylmethyl]propionic Acid (PDMA), acrylic acid, methacrylic acid, beta carboxyethylacrylate, mono-2-(methacryloxy)ethyl succinate, and mono-2-(methacryloxy) ethyl maleate.

Combinations of such acids are also desirable to impart organic compatibility and reactivity. Other suitable acid mixtures useful for surface treatment of the heavy metal oxide can include aliphatic carboxylic acids such as, for example, oleic acid, stearic acid, and octanoic acid, aromatic nonreactive acids such as methoxy phenyl acetic acid and 3,4,5 triethoxy benzoic acid, as well as itaconic acid, toluene sulfonic acid, ethylene glycol methacrylate phosphate, the salts of the acids just stated, and blends thereof.

Surface treated heavy metal oxide particles can be combined with surface treated non-heavy metal oxide particles to provide fillers to be incorporated into a hardenable resin. The combined weight of surface treated non-heavy metal oxide and heavy metal oxides are preferably present in the dental materials on amounts ranging from about 10% to 95% based on the total weight of the dental material. More preferably, the combined weights of such treated non-heavy metal oxide and heavy metal oxides are present in an amount of 50% to 85% of the weight of the material; most preferably in an amount of 60% to 80%. The weight of surface treated heavy metal oxides may represent 0.1% to 95% of the combined surface treated non-heavy metal oxide and heavy metal oxide weight, with the remaining weight constituted by surface treated non-heavy metal oxide. More preferably, the surface treated heavy metal oxide would constitute 5%–70% of the combined surface treated non-heavy metal oxide and heavy metal oxide material weight and most preferably 15%–40%.

Alternatively, in place of or in addition to the non-heavy metal oxide particles and heavy metal oxide as described herein, a filler comprising a substantially amorphous cluster of non-heavy metal oxide and a heavy metal oxide can be used as in the dental materials of the invention. This preferred cluster is taught by Zhang et al. in U.S. patent application Ser. No. 09/428,830, filed on Oct. 28, 1999. The amorphous cluster of U.S. patent application Ser. No. 09/428,830, filed on Oct. 28, 1999, preferably has an average diameter of less than about 5 $\mu$m. More preferably, the cluster has an average diameter of less than 2 $\mu$m.

As disclosed in U.S. patent application Ser. No. 09/428,830, filed on Oct. 28, 1999, a "cluster" refers to the nature of the association among the non-heavy metal oxide particles present in the cluster. Typically, the non-heavy metal oxide particles of the clusters are associated by relatively weak intermolecular forces that cause the non-heavy metal oxide particles to clump together, even when dispersed in a hardenable resin for a dental material. To the extent that the heavy metal oxide is present in the cluster as particles, the heavy metal oxide particles display a similar association to each other and to the non-heavy metal oxide particles.

By "substantially amorphous" it is meant that the clusters are essentially free of crystalline structure. Absence of crystallinity (or presence of amorphous phases) is preferably determined by a procedure that provides a Crystallinity Index, as described below in the Test Methods. The Crystallinity Index characterizes the extent a material is crystalline or amorphous, whereby a value of 1.0 is indicative of a fully crystalline structure, and a value near zero indicates presence of amorphous phase only. The fillers of the invention preferably have an index of less than about 0.1; more preferably less than about 0.05.

The clusters useful for the materials of the invention are preferably not fully densified. The term "fully dense," as used herein, is descriptive of a particle that is near theoretical density, having substantially no open porosity detectable by standard analytical techniques such as the B.E.T. nitrogen technique (based upon adsorption of $N_2$ molecules from a gas with which a specimen is contacted). Such measurements yield data on the surface area per unit weight of a sample (e.g. $m^2/g$ which can be compared to the surface area per unit weight for a mass of perfect microspheres of the same size to detect open porosity. Such measurements may be made on a Quantasorb apparatus made by Quantachrome Corporation of Syosett, N.Y. Density measurements may be made using an air, helium or water pycnometer.

The clusters useful for the invention, as described in U.S. patent application Ser. No. 09/428,830, filed on Oct. 28, 1999, are often manufactured in process that includes heat treatment. The surface area of the cluster after heat treatment compared to its surface area before heat treatment, is preferably quite high. The ratio of the surface area of the heat treatment compared to the surface area before heat treatment is preferably greater than about 50%, more preferably greater than about 80%.

The non-heavy metal oxide particles used in the clusters preferably have an average diameter of less than about 100 nm; more preferably, the particles are less than about 50 nm in average diameter. In a preferred embodiment silica particles are used in the clusters. Silica particles are preferably made from an aqueous colloidal dispersion of silica (i.e., a sol or aquasol). The colloidal silica is typically in the concentration of about 1 to 50 weight percent in the silica sol. Colloidal silica sols which can be used in preparing the fillers of the invention are available commercially having different colloid sizes, see Surface & Colloid Science, Vol. 6, ed. Matijevic, E., Wiley Interscience, 1973. Preferred silica sols for use in making the clusters of the invention are those which are supplied as a dispersion of amorphous silica in an aqueous medium (such as the Nalco colloidal silicas made by Nalco Chemical Company) and those which are low in sodium concentration and can be acidified by admixture with a suitable acid (e.g. Ludox colloidal silica made by E. I. DuPont de Nemours & Co. or Nalco 2326 from Nalco Chemical Co.). Preferably, the silica particles in the sol have an average particle diameter of about 5–100 nm, more preferably 10–50 nm, most preferably, 12–40 nm. A particularly preferred silica sol is NALCO 1042.

Preferably, the heavy metal oxide is provided in the form of particles. The heavy metal oxide particles preferably have an average diameter of less than about 100 nm. More preferably, the particles are less than about 50 nm; most preferably less than about 10 nm in average diameter. The heavy metal oxide particles may be aggregated. If so, it is preferred that the aggregated particles are less than about 100 nm, and more preferably are less than about 50 nm in average diameter.

The heavy metal oxide precursor useful in making the heavy metal oxide component used in the fillers and materials of the invention can be organic or inorganic acid or water soluble salts, such as the heavy metal salts of aliphatic mono or dicarboxylic acids (e.g. formic, acetic, oxalic, citric, tartaric, and lactic acids). Preferred heavy metal compounds contain zirconium. Zirconyl acetate compounds are particularly preferred. Useful inorganic zirconium compounds which can be used are zirconium oxynitrate and zirconium oxychloride. See U.S. Pat. No. 3,709,706, Column 4, line 61–Column 5, line 5 for further details on zirconia sources which can be used in this invention. A particularly preferred zirconyl acetate is available from MEI (Magnesium Elektron, Flemington, N.J.).

The clusters useful in the present invention are preferably treated with a resin-compatibilizing surface treatment agent. Particularly preferred surface treatment or surface modifying agents include silane treatment agents capable of polymerizing with a resin. Preferred silane treatment agent include γ-methacryloxylpropyltrimethoxysilane, available commercially under the trade designation A-174, available commercially from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful in treating the cluster, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic function subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, aryl polyethers, alkyl, hydroxy alkyl, hydroxy aryl, or amino alkyl functional silanes.

The dental materials of the present invention include a hardenable resin. These resins preferably are generally thermosetting resins capable of being hardened to form a polymer network such as, for example, acrylate resins, methacrylate resins, epoxy resins, and vinyl resins. Preferably, the hardenable resin is made from one or more matrix-forming oligomer, monomer, or polymer, or blends thereof.

In a preferred embodiment where the dental material of the invention is a dental composite, polymerizable resins suitable for use include hardenable organic resins having sufficient strength, hydrolytic stability, and non-toxicity to render them suitable for use in the oral environment. Examples of such resins include acrylate, methacrylate, urethane, carbamoylisocyanurate and epoxy resins, e.g., those shown in U.S. Pat. Nos. 3,066,112, 3,539,533, 3,629,187, 3,709,866, 3,751,399, 3,766,132, 3,860,556, 4,002,669, 4,115,346, 4,259,117, 4,292,029, 4,308,190, 4,327,014, 4,379,695, 4,387,240 and 4,404,150, and mixtures and derivatives thereof.

One class of preferred hardenable resins are materials having free radically active functional groups and include monomers, oligomers, and polymers having one or more ethylenically unsaturated groups. Alternatively, the hardenable resin can be a material from the class of resins that include cationically active functional groups. In another alternative, a mixture of hardenable resins that include both cationically curable and free radically curable resins may be used for the dental materials of the invention.

In the class of hardenable resins having free radically active functional groups, suitable materials for use in the invention contain at least one ethylenically unsaturated bond, and are capable of undergoing addition polymerization. Such free radically polymerizable materials include mono-, di- or poly- acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200–500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

For free radical polymerization (hardening), an initiation system can be selected from systems which initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically an be capable of generating free radicals for addition polymerization upon exposure to light energy having a wavelength between 200 and 800 nm.

A variety of visible or near-IR photoinitiator systems may be used for photopolymerization of free-radically polymerizable materials useful in the invention. For example, in free radical polymerization (hardening), a photoinitiation system can be selected from systems which initiate polymerization via a two component system of an amine and an α-diketone as described in U.S. Pat No. 4,071,424, which is herein incorporated by reference. Alternatively, the resin can be combined with a three component or ternary photoinitiator system such as described in U.S. Pat No. 5,545,676 which is incorporated herein by reference.

In the ternary photoinitiator system, the first component is an iodonium salt, i.e., a diaryliodonium salt. The iodonium salt is preferably soluble in the monomer and shelf-stable (i.e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. Nos. 3,729,313, 3,741,769, 3,808,006, 4,250,053 and 4,394,403, the iodonium salt disclosures of which are incorporated herein by reference. The iodonium salt can be a simple salt (e.g., containing an anion such as Cl$^-$, Br$^-$, I$^-$ or $C_4 H_5 SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, more preferably greater than 400 to 700 nanometers and most preferably greater than 400 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

Suitable sensitizers can include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring high sensitivity, it is preferred to employ a sensitizer containing a julolidinyl moiety. For applications requiring deep cure (e.g., cure of highly-filled composites), it is preferred to employ sensitizers having an extinction coefficient below about 1000, more preferably below about 100, at the desired wavelength of irradiation for photopolymerization. Alternatively, dyes that exhibit reduction in light absorption at the excitation wavelength upon irradiation can be used.

For example, a preferred class of ketone sensitizers has the formula:

where X is CO or $CR^5R^6$, where $R^5$ and $R^6$ can be the same or different, and can be hydrogen, alkyl, alkaryl or aralkyl, b is zero or one, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'- 3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676, which is incoporated herein by reference.

Alternatively, free-radical initiators useful in the invention include the class of acylphosphine oxides, as described in European Patent Application No. 173567, U.S. Pat. No. 4,737,593 and United Kingdom Pat No. GB 2,310,855. Such acylphosphine oxides are of the general formula

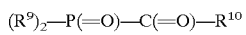

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S—, O—, or N—containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms.

Preferred acylphosphine oxides useful in the invention are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide (IRGACURE™ 819, Ciba Specialty Chemicals, Tarrytown, N.Y.).

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. The initiator can be employed in catalytically-effective amounts, such as from about 0.1 to about 5 weight percent, based on the weight of ethylenically-unsaturated compound present, of the acylphosphine oxide plus from about 0.1 to about 5 weight percent, based on the weight of ethylenically-unsaturated compound present, of the tertiary amine.

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis($\eta^5$-2,4-cyclopentadien-1-yl)-bis(2,6-difluoro-3-(1H-pyrrol-1-yl)phenyl)titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Another free-radical initiator system that can alternatively be used in the dental materials of the invention includes the class of ionic dye—counterion complex initiators comprising a borate anion and a complementary cationic dye.

Borate salt photoinitiators are described, for example, in U.S. Pat. Nos. 4,772,530, 4,954,414, 4,874,450, 5,055,372, and 5,057,393, the disclosures of which are incorporated herein by reference. Borate anions useful in these photoinitiators generally can be of the formula $R^1R^2R^3R^4B^-$ wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium. Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,10-phenanthroline, 3,4,7,8-tetramethylphenanthroline, 2,4,6-tri(2-pyridyl-s-triazine) and related ligands.

Yet another alternative class of initiators capable of initiating polymerization of free radically active functional groups includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least 40° C. to 15° C. under normal conditions or at elevated pressure. This procedure is preferred for initiating polymerization of materials occurring outside of the oral environment.

Yet another alternative class of initiators capable of initiating polymerization of free radically active functional groups that are useful for the dental materials of the invention are those that include free radical-generating thermal initiators. Examples include peroxides such as, for example, benzoyl peroxide and lauryl peroxide, and azo compounds such as, for example, 2,2-azobis-isobutyronitrile (AIBN).

An alternative class of hardenable resins useful in the dental materials of the invention may include cationically active functional groups. Materials having cationically active functional groups include polymerizable epoxy resins, vinyl ethers, oxetanes, spiro-orthocarbonates, spiro-orthoesters, and the like.

Preferred materials having cationically active functional groups are epoxy resins. Such materials are organic compounds having an oxirane ring, i.e., a group of the formula

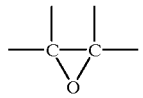

which is polymerizable by ring opening. These materials include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The "average" number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexane oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl)adipate. For a more detailed list of useful epoxides of this nature, reference is made to the U.S. Pat. No. 3,117,099, which is incorporated herein by reference.

Further epoxy-containing materials which are useful in the compositions of this invention include glycidyl ether monomers of the formula

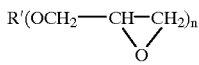

where R' is alkyl or aryl and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type are described in U.S. Pat. No. 3,018,262, which is incorporated herein by reference, and in "Handbook of Epoxy Resins" by Lee and Neville, McGraw-Hill Book Co., New York (1967).

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins are well known and contain such epoxides as epichlorohydrins, alkylene oxides, e.g., propylene oxide, styrene oxide; alkenyl oxides, e.g., butadiene oxide; glycidyl esters, e.g., ethyl glycidate.

Blends of various epoxy-containing materials are also contemplated. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar.

There are a host of commercially available epoxy resins which can be used in this invention. In particular, epoxides which are readily available include octadecylene oxide, epichlorohydrin, styrene oxide, vinylcyclohexene oxide, glycidol, glycidyl methacrylate, diglycidyl ether of Bisphenol A (e.g., those available under the trade designations "Epon 828", "Epon 825", "Epon 1004" and "Epon 1010" from Shell Chemical Co., "DER-331", "DER-332", and "DER-334", from Dow Chemical Co.), vinylcyclohexene dioxide (e.g., "ERL-4206" from Union Carbide Corp.), 3,4-epoxycyclohexylmethyl-3,4-epoxycyclohexene carboxylate (e.g., "ERL-4221" or "CYRACURE UVR 6110" or "UVR 6105" from Union Carbide Corp.), 3,4-epoxy-6-methylcyclohexylmethyl-3,4-epoxy-6-methyl-cyclohexene carboxylate (e.g., "ERL-4201" from Union Carbide Corp.), bis(3,4-epoxy-6-methylcyclohexylmethyl)adipate (e.g., "ERL-4289" from Union Carbide Corp.), bis(2,3-epoxycyclopentyl)ether (e.g., "ERL-0400" from Union Carbide Corp.), aliphatic epoxy modified from polypropylene glycol (e.g., "ERL-4050" and "ERL-4052" from Union Carbide Corp.), dipentene dioxide (e.g., "ERL-4269" from Union Carbide Corp.), epoxidized polybutadiene (e.g., "Oxiron 2001" from FMC Corp.), silicone resin containing epoxy functionality, flame retardant epoxy resins (e.g., "DER-580", a brominated bisphenol type epoxy resin available from Dow Chemical Co.), 1,4-butanediol diglycidyl ether of phenolformaldehyde novolak (e.g., "DEN-431" and "DEN-438" from Dow Chemical Co.), and resorcinol diglycidyl ether (e.g., "Kopoxite" from Koppers Company, Inc.), bis(3,4-epoxycyclohexyl)adipate (e.g., "ERL-4299" or "UVR-6128", from Union Carbide Corp.), 2-(3,4-epoxycyclohexyl-5,5-spiro-3,4-epoxy)cyclohexane-meta-dioxane (e.g., "ERL-4234" from Union Carbide Corp.), vinylcyclohexene monoxide 1,2-epoxyhexadecane (e.g., "UVR-6216" from Union Carbide Corp.), alkyl glycidyl ethers such as alkyl $C_8$–$C_{10}$ glycidyl ether (e.g., "HELOXY Modifier 7" from Shell Chemical Co.), alkyl $C_{12}$–$C_{14}$ glycidyl ether (e.g., "HELOXY Modifier 8" from Shell Chemical Co.), butyl glycidyl ether (e.g., "HELOXY Modifier 61" from Shell Chemical Co.), cresyl glycidyl ether (e.g., "HELOXY Modifier 62" from Shell Chemical Co.), p-ter butylphenyl glycidyl ether (e.g., "HELOXY Modifier 65" from Shell Chemical Co.), polyfunctional glycidyl ethers such as diglycidyl ether of 1,4-butanediol (e.g., "HELOXY Modifier 67" from Shell Chemical Co.), diglycidyl ether of neopentyl glycol (e.g., "HELOXY Modifier 68" from Shell Chemical Co.), diglycidyl ether of cyclohexanedimethanol (e.g., "HELOXY Modifier 107" from Shell Chemical Co.), trimethylol ethane triglycidyl ether (e.g., "HELOXY Modifier 44" from Shell Chemical Co.), trimethylol propane triglycidyl ether (e.g., "HELOXY Modifier 48" from Shell Chemical Co.), polyglycidyl ether of an aliphatic polyol (e.g., "HELOXY Modifier 84" from Shell Chemical Co.), polyglycol diepoxide (e.g., "HELOXY Modifier 32" from Shell Chemical Co.), bisphenol F epoxides (e.g., "EPN-1138" or "GY-281" from Ciba-Geigy Corp.), 9,9-bis[4-(2,3-epoxypropoxy)-phenyl]fluorenone (e.g., "Epon 1079" from Shell Chemical Co.).

It is also within the scope of this invention to use one or more epoxy resins blended together. The different kinds of resins can be present in any proportion.

Optionally, monohydroxy- and polyhydroxy-alcohols may be added to the curable compositions of the invention, as chain-extenders for the epoxy resin. The hydroxyl-containing material used in the present invention can be any organic material having hydroxyl functionality of at least 1, and preferably at least 2.

Preferably the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e., from about 32 to 200, intermediate molecular weight, i.e., from about 200 to 10,000, or high molecular weight, i.e., above about 10,000. As used herein, all molecular weights are weight average molecular weights.

The hydroxyl-containing material can optionally contain other functionalities that do not substantially interfere with cationic cure at room temperature. Thus, the hydroxyl-containing materials can be nonaromatic in nature or can contain aromatic functionality. The hydroxyl-containing material can optionally contain heteroatoms in the backbone of the molecule, such as nitrogen, oxygen, sulfur, and the like, provided that the ultimate hydroxyl-containing material does not substantially interfere with cationic cure at room temperature. The hydroxyl-containing material can, for example, be selected from naturally occurring or synthetically prepared cellulosic materials. Of course, the hydroxyl-containing material is also substantially free of groups which may be thermally or photolytically unstable; that is, the material will not decompose or liberate volatile components at temperatures below about 100° C. or in the presence of actinic light which may be encountered during the desired curing conditions for the photocopolymerizable composition. Useful hydroxyl-containing materials are described, for example, in U.S. Pat. No. 5,856,373, which is incorporated herein by reference.

The amount of hydroxyl-containing organic material used in the compositions of the invention may vary over broad ranges, depending upon factors such as the compatibility of the hydroxyl-containing material with the epoxide, the equivalent weight and functionality of the hydroxyl-containing material, the physical properties desired in the final cured composition, the desired speed of photocure, and the like.

Blends of various hydroxyl-containing materials may be useful in the dental materials of the invention. Examples of such blends include two or more molecular weight distributions of hydroxyl-containing compounds, such as low molecular weight (below 200), intermediate molecular weight (about 200 to 10,000) and higher molecular weight (above about 10,000). Alternatively or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

For hardening resins comprising cationically active functional groups, an initiation system can be selected from systems which initiate polymerization via radiation, heat, or redox/auto-cure chemical reaction. For example, epoxy polymerization may be accomplished by the use of thermal curing agents, such as anhydrides or amines. A particularly useful example of an anhydride curing agent would be cis-1,2-cyclohexanedicarboxylic anhydride.

Alternatively and preferably, initiation systems for resins comprising cationically active functional groups are those that are photoactivated. Photoactive cationic nuclei, photo-active cationic moieties, and photoactive cationic organic compounds are art recognized classes of materials as exemplified by U.S. Pat. Nos. 4,250,311; 3,708,296; 4,069,055; 4,216,288; 5,084,586; 5,124,417; 4,985,340, 5,089,536, and 5,856,373, each of which is incorporated herein by reference.

The cationically-curable materials can be combined with a three component or ternary photoinitiator system, as described above. Three component initiator systems are also described in U.S. patent application Ser. Nos. 08/838,835, and 08/840,093, both of which are now allowed, each of which is incorporated herein by reference.

For hardening cationically curable resins, examples of useful aromatic iodonium complex salts (i.e. the first component of the ternary photoinitiator system) include: diphenyliodonium tetrafluoroborate; di(4-methylphenyl) iodonium tetrafluoroborate; phenyl-4-methylphenyliodonium tetrafluoroborate; di(4-heptylphenyl)iodonium tetrafluoroborate; di(3-nitrophenyl) iodonium hexafluorophosphate; di(4-chlorophenyl) iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl)iodonium hexafluorophosphate; diphenyliodonium hexafluoroarsenate; di(4-phenoxyphenyl) iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl)iodonium hexafluorophosphate; di(4-bromophenyl)iodonium hexafluorophosphate; di(4-methoxyphenyl)iodonium hexafluorophosphate; di(3-carboxyphenyl)iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate (DPISbF$_6$).

Of the aromatic iodonium complex salts which are suitable for use in the compositions of the invention diaryliodonium hexafluorophosphate and diaryliodonium hexafluoroantimonate are among the preferred salts. These salts are preferred because, in general, they promote faster reaction, and are more soluble in inert organic solvents than are other aromatic iodonium salts of complex ions.

As mentioned above, the second and third component of the ternary photoinitiator system is a sensitizer and an electron donor, respectively. The sensitizers useful in cationic polymerization of the dental materials of the invention are those that are described above for the free-radically cured materials. Similarly, the electron donor useful for cationic polymerization of the materials of the invention include those that are described above for the free-radically cured materials. However, in the case of cationically cured materials, the electron donor preferably meets the requirements set forth in U.S. application Ser. Nos. 08/838,835, and 08/840,093, both of which are now allowed, each of which is incorporated herein by reference, and are soluble in the polymerizable composition. The donor can also be selected in consideration of other factors, such as shelf stability and the nature of the polymerizable materials, iodonium salt and sensitizer chosen. A class of donor compounds that may be useful in the inventive systems may be selected from some of the donors described in U.S. Pat. No. 5,545,676.

The donor is typically an alkyl aromatic polyether or an N-alkyl arylamino compound wherein the aryl group is substituted by one or more electron withdrawing groups. Examples of suitable electron withdrawing groups include carboxylic acid, carboxylic acid ester, ketone, aldehyde, sulfonic acid, sulfonate and nitrile groups.

A preferred group of N-alkyl arylamino donor compounds is described by the following structural formula:

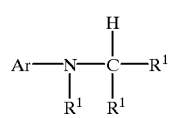

wherein each $R^1$ is independently H, $C_{1-18}$ alkyl that is optionally substituted by one or more halogen, —CN, —OH, —SH, $C_{1-18}$ alkoxy, $C_{1-18}$ alkylthio, $C_{3-18}$ cycloalkyl, aryl, COOH, COO$C_{1-18}$ alkyl, ($C_{1-18}$ alkyl)$_{0-1}$—CO—$C_{1-18}$ alkyl, SO$_3R^2$, CN or an aryl group that is optionally substituted by one or more electron withdrawing groups, or the $R^1$ groups may be joined to form a ring; and Ar is aryl that is substituted by one or more electron withdrawing groups. Suitable electron withdrawing groups include —COOH, —COOR$^2$, —SO$_3$R$^2$, —CN, —CO—C$_{1-18}$ alkyl and —C(O)H groups, wherein R$^2$ can be a C$_{1-18}$ straight-chain, branched, or cyclic alkyl group.

A preferred group of aryl alkyl polyethers has the following structural formula:

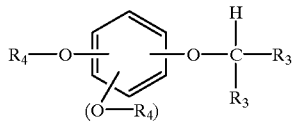

wherein n=1–3 each $R^3$ is independently H or C$_{1-18}$ alkyl that is optionally substituted by one or more halogen, —CN, —OH, —SH, C$_{1-18}$ alkoxy, C$_{1-18}$ alkylthio, C$_{3-18}$ cycloalkyl, aryl, substituted aryl, —COOH, —COOC$_{1-18}$ alkyl, —(C$_{1-18}$ alkyl)$_{0-1}$—COH, —(C$_{1-18}$ alkyl)$_{0-1}$—CO—C$_{1-18}$ alkyl, —CO—C$_{1-18}$ alkyl, —C(O)H or —C$_{2-18}$ alkenyl groups and each $R^4$ can be C$_{1-18}$ alkyl that is optionally substituted by one or more halogen, —CN, —OH, —SH, C$_{1-18}$ alkoxy, C$_{1-18}$ alkylthio, C$_{3-18}$ cycloalkyl, aryl, substituted aryl, —COOH, —COOC$_{1-18}$ alkyl, —(C$_{1-18}$ alkyl)$_{0-1}$—COH, —(C$_{1-18}$ alkyl)$_{0-1}$—CO—C$_{1-18}$ alkyl, —CO—C$_{1-18}$ alkyl, —C(O)H or —C$_{2-18}$ alkenyl groups.

In each of the above formulas the alkyl groups can be straight-chain or branched, and the cycloalkyl group preferably has 3 to 6 ring carbon atoms but may have additional alkyl substitution up to the specified number of carbon atoms. The aryl groups may be carbocyclic or heterocyclic aryl, but are preferably carbocyclic and more preferably phenyl rings.

Preferred donor compounds include 4-dimethylaminobenzoic acid, ethyl 4-dimethylaminobenzoate, 3-dimethylaminobenzoic acid, 4-dimethylaminobenzoin, 4-dimethylaminobenzaldehyde, 4-dimethylaminobenzonitrile and 1,2,4-trimethoxybenzene.

An alternative photoinitiator system for cationic polymerizations includes the use of organometallic complex cations essentially free of metal hydride or metal alkyl functionality selected from those described in U.S. Pat. No. 4,985,340, and such description is incorporated herein by reference and has the formula:

$$[(L^1)(L^2)M]^{+q} \qquad (1)$$

wherein

M represents a metal selected from the group consisting of Cr, Mo, W, Mn, Re, Fe, Ru, Os, Co, Rh, Ir, Pd, Pt and Ni, preferably Cr, Mo, W, Mn, Fe, Ru, Co, Pd, and Ni; and most preferably Mn and Fe;

$L^1$ represents 1 or 2 cyclic, polyunsaturated ligands that can be the same or different ligand selected from the group consisting of substituted and unsubstituted cyclopentadienyl, cyclohexadienyl, and cycloheptatrienyl, cycloheptatriene, cyclooctatetraene, heterocyclic compounds and aromatic compounds selected from substituted or unsubstituted arene compounds and compounds having 2 to 4 fused rings, and units of polymers, e.g., a phenyl group of polystyrene, poly(styrene-co-butadiene), poly(styrene-co-methyl methacrylate), poly(a-methylstyrene), and the like; a cyclopentadiene group of poly(vinylcyclopentadiene); a pyridine group of poly(vinylpyridine), and the like, each capable of contributing 3 to 8 electrons to the valence shell of M;

$L^2$ represents none, or 1 to 3 nonanionic ligands contributing an even number of electrons that can be the same or different ligand selected from the group of carbon monoxide, ketones, olefins, ethers, nitrosonium, phosphines, phosphites, and related derivatives of arsenic and antimony, organonitriles, amines, alkynes, isonitriles, dinitrogen, with the proviso that the total electronic charge contributed to M results in a net residual positive charge of q to the complex;

q is an integer having a value of 1 or 2, the residual charge of the complex cation.

Organometallic salts are known in the art and can be prepared as described in, for example, EPO No. 094,914 and U.S. Pat. Nos. 5,089,536, 4,868,288, and 5,073,476, and such descriptions are incorporated herein by reference.

Examples of preferred cations include:

diphenyliodonium, ditolyliodonium, didodecylphenyliodonium, (4-octyloxyphenyl) phenyliodonium, and bis(methoxyphenyl)iodonium;

triphenylsulfonium, diphenyl-4-thiophenoxyphenylsulfonium, and 1,4-phenylene-bis (diphenylsufonium);

bis($\eta^5$-cyclopentadienyl)iron(1+), bis($\eta^5$-methylcyclopentadienyl)iron (1+), ($\eta^5$-cyclopentadienyl)($\eta^5$-methylcyclopentadienyl)iron (1+), and bis($\eta^5$-trimethylsilylcyclopentadienyl)iron (1+);

bis(72 $^6$-xylenes)iron (2+), bis($\eta^6$-mesitylene)iron (2+), bis($\eta^6$-durene)iron (2+), bis($\eta^6$-pentamethylbenzene)iron (2+), and bis($\eta^6$-dodecylbenzene) iron (2+);

($\eta^5$-cyclopentadienyl)($\eta^6$-xylenes)iron(1+), commonly abbreviated as (CpFeXy)( 1+), ($\eta^5$-cyclopentadienyl)($\eta^6$-toluene)iron(1+),
($\eta^5$-cyclopentadienyl)($\eta^6$-mesitylene)iron(1+),
($\eta^5$-cyclopentadienyl)($\eta^6$-pyrene)iron(1+),
($\eta^5$-cyclopentadienyl)($\eta^6$-naphthalene)iron(1+), and
($\eta^5$-cyclopentadienyl)($\eta^6$-dodecylphenyl)iron(1+).

Alternatively, hardenable resins useful for the invention may have both cationically active and free radically active functional groups contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the "Cyclomer" series, such as Cyclomer M-100, M-101, or A-200 available from Daicel Chemical, Japan, and Ebecryl-3605 available from Radcure Specialties.

The photoinitiator compounds are preferably provided in the dental materials of the invention in an amount effective to initiate or enhance the rate of cure or hardening of the resin system. Photopolymerizable compositions useful in the invention are prepared by simply admixing, under "safe light" conditions, the components as described above. Suitable inert solvents may be employed if desired when effecting this mixture. Any solvent may be used which does not react appreciably with the components of the inventive compositions. Examples of suitable solvents include acetone, dichloromethane, and acetonitrile. A liquid material to be polymerized may be used as a solvent for another liquid or solid material to be polymerized. Solventless compositions can be prepared by simply dissolving an aromatic iodonium complex salt and sensitizer in an epoxy resin-polyol mixture with or without the use of mild heating to facilitate dissolution.

Various methods can be employed to combine the sol (particles) and the hardenable resin. The objectives in the preparation are to facilitate the surface modification of the particles and to remove the water, excess solvent and/or salt by-products.

Generally, the process of making the dental materials of the invention involve surface modification of the particles followed by incorporation of the particles into the hardenable resin. The surface modification process involves the mixture of an inorganic sol with surface modifying agents. Optionally, a co-solvent can be added at this point, such as for example, methoxy propanol. The co-solvent can enhance the solubility of the surface modifying agents as well as the surface modified particles. The mixture comprising the inorganic sol and surface modifying agents is subsequently reacted at room or an elevated temperature, with or without mixing. In a preferred method, the mixture can be reacted at about 85 C. for about 24 hours, resulting in the surface modified sol. In a preferred method, where heavy metal oxides are included in the material of the composition, the surface treatment of the optional heavy metal oxide can preferably involve the adsorption of acidic molecules to the particle surface. The surface modification of the heavy metal oxide preferably takes place at room temperature.

The surface modified particles of non-heavy metal alone or in combination with the heavy metal oxide can then be incorporated into the hardenable resin in various methods. In one aspect, a solvent exchange procedure is utilized whereby the resin is added to the surface modified sol, followed by removal of the water and co-solvent (if used) via evaporation, thus leaving the particles dispersed in the hardenable resin. The evaporation step can be accomplished for example, via distillation, rotary evaporation or oven drying.

In another aspect, the surface modified particles can be extracted into a water immiscible solvent followed by solvent exchange, if so desired.

Alternatively, another method for incorporating the non-heavy metal oxide particles, the heavy metal oxide, and the hardenable resin involves the drying of the modified particles into a powder, followed by the addition of the resin material into which the particles are dispersed. The drying step in this method can be accomplished by conventional means suitable for the system, such as, for example, oven drying or spray drying. Where a spray drying technique is utilized, the inlet temperature is preferably at about 200° C. and the outlet temperature is preferably between about 85° C. to 100° C. In another aspect, conventional oven drying can be performed at between about 70° C. to 90° C. for about 2 to 4 hours.

Alternatively, in yet another aspect, the surface modified particles can be filtered to obtain solids which can be dried into a powder. This method is preferred when the particles of the surface modified aqueous sol have agglomerated due to the incompatibility of the surface treatment with the aqueous medium. The hardenable resin is then added to the dry, filtered particles to obtain the dental materials of the invention.

The dental materials of the present invention may optionally comprise additional adjuvants suitable for use in the oral environment, including colorants, flavorants, antimicrobials, fragrance, stabilizers, viscosity modifiers and fluoride releasing materials. For example, a fluoride releasing glass may be added to the materials of the inventiont to provide the benefit of long-term release of fluoride in use, for example in the oral cavity. Fluoroaluminosilicate glasses are particularly preferred. Particularly preferred are silanol treated fluoroaluminosilicate glass fillers, as described in U.S. Pat. No. 5,332,429, the disclosure of which is expressly incorporated by reference herein. Other suitable adjuvants include agents that impart fluorescence and/or opalescence.

In a preferred method of using the dental material of the invention, comprising a hardenable resin and fillers of the invention, the material is placed near or on a tooth surface, followed by a manipulation by the practitioner or laboratory to change the topography of the material, then hardening the resin. These steps can be followed sequentially or in a different order. For example, in a preferred embodiment where the dental material is a mill blank or a prosthesis, the hardening step is generally completed prior to changing the topography of the material. Changing the topography of the material can be accomplished in various ways, such as carving or manual manipulation using hand held instruments, or by machine or computer aided apparatus, such as a CAD/CAM milling machine in the case of prostheses and mill blanks. Optionally, a finishing step can be performed to polish, finish, or apply a coating on the dental material.

The following examples are given to illustrate, but not limit, the scope of this invention. Unless otherwise indicated, all parts and percentages are by weight.

Test Methods

Average Particle Diameter Determination

Cured dental material approximately 80 nm thick are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 Kv. A population size of about 50–100 particles can be measured and an average diameter is determined.

Diametral Tensile Strength (DTS) and Compressive Strength (CS) Testing

ADA "American Dental Association") specification No. 9 and ADA specification No. 27 respectively of ISO-test procedure 4049 (1988) were followed for all DTS and CS testing. Specifically, for determination of compressive strength ("CS") and diametral tensile strength ("DTS"), the composition was packed into a 4 mm inside diameter glass tube, capped with silicone rubber plugs and axially compressed at about 0.28 MPa for 15 minutes, then light cured for 80 seconds by exposure to two oppositely-disposed Visilux 2™ (3M Co , St. Paul, Minn.) units. Each sample was then irradiated for 90 seconds using a Dentacolor XS unit (Kulzer, Inc., Germany). Cured samples were cut on a diamond saw to form cylindrical plugs 8 mm long for measurement of CS and 2 mm long for measurement of DTS. The plugs were stored in distilled water at 37° C. for 24 hours. CS and DTS values for each composition were measured using an Instron™ (Instron 4505, Instron Corp. Canton, Mass.).

The compressive strength (CS) of these samples was tested on an Instron with 10 kN load cell. A total of 5 cylinders of cured composite with about 8 mm length and 4 mm diameter were prepared.

The Diametral Tensile Strength (DTS) of these samples was tested on an Instron with 10 kN load cell. A total of 5 cylinders of cured composite with about 2 mm length and 4 mm diameter were prepared.

Visual Opacity and Radiopacity Testing

Disc-shaped 1 mm thick by 20 mm diameter samples of the composite were cured by exposing them to illumination from an Visilux 2™ (3M Co, St. Paul, Minn.) curing light for 60 seconds on each side of the disk at a distance of 6 mm. The cured composite samples were then evaluated for visual opacity and radiopacity as follows.

tially as shown in Table A, using a Buehler ECOMET 4 Polisher with an AUTOMET 2 Polishing Head. A flat test surface with Ra roughness of less than 25 nm was produced, the largest acceptable starting Ra for the toothbrushing abrasion resistance test as calculated according to the procedures described in "Perthometer, Surface Texture Parameters" (Mahr GMBH, Gottingen, Germany ed. Sep. 01, 1999).

TABLE A

Polishing Steps

| Step # | Surface | Abrasive | Lubricant | Force (N/sample) | Platen Rotation | Speed (rpm) | Time |
|---|---|---|---|---|---|---|---|
| 1 | SiC | 120 grit | Water | 22 N/smpl | Complete | 150 | (:20) 2× |
| 2 | SiC | 320 grit | Water | 22 N/smpl | Complete | 150 | (:20) |
| 3 | SiC | 600 grit | Water | 22 N/smpl | Complete | 150 | (:20) 2× |
| 4 | Polimet* | 15 µm Metadi Diamond Susp* | Metadi Fluid Extender* | 22 N/smpl | Complete | 150 | (1:30) (1:00) |
| 5 | Polimet* | 9 µm Metadi Diamond Susp* | Metadi Fluid Extender* | 22 N/smpl | Complete | 150 | (2:00) 2× |
| 6 | Textmet* | 3 µm Metadi Diamond Susp* | Metadi Fluid Extender* | 22 N/smpl | Complete | 150 | (2:00) (1:00) |
| 7 | Microcloth* | Master-polish* | Water | 9 N/smpl | Complete | 100 | (2:00) (1:30) |

*Registered trademark of Buehler, LTD

Cured composite samples were measured for direct light transmission by measuring transmission of light through the thickness of the disk using a MacBeth transmission densitometer Model TD-903 equipped with a visible light filter, available from MacBeth (MacBeth, Newburgh, N.Y.).

For radiopacity evaluation, the procedure used followed the ISO-test procdeure 4049 (1988). Specifically, cured composite samples were exposed to radiation using a Gendex GX-770 dental X-ray (Milwaukee, Wis.) unit for 0.73 seconds at 7 milliamps and 70 kV peak voltage at a distance of about 400 millimeters. The X-ray negative was developed using a Air Techniques Peri-Pro automatic film processor. (Hicksville, N.Y.).

Toothbrush Abrasion Resistance Test

A rectangular 20×9×3 mm thick paste of each example was cured with a Visilux 2™ (3M Co., St. Paul, Minn.) for 60 seconds followed by additional curing for 90 seconds in a Dentacolor™ XS light box (Kulzer, Inc., Germany).

Preparation of the examples for the Toothbrush Abrasion Resistance Test was based on the guidelines in ASTM-E3-95 "Standard Practice for Preparation of Metallographic Specimens." The specifics for each step, as shown in Table A, were chosen to produce the best final polish for the examples. One face of each example was Au/Pd coated with a Denton Desk II Cold Sputter/Etch Unit (Denton Vacuum, Inc. Moorestown, N.J.) (30 seconds, 2 sputters, 30 mA) to insure adequate adhesion to the epoxy. Each example was placed into cylindrical 31.75 mm by 19.05 mm deep molds. The molds were filled with Buehler's Epoxide™ (Buehler Ltd., Lake Bluff, Ill.) and allowed to cure for 24 hours. The mounted examples were polished according to the following procedure where a series of steps were performed sequen- The surface of each of the examples was cleaned with Isopropyl and placed into an ultrasonic cleaner for approximately 60 seconds between each step to avoid contamination.

The lower half of each rectangular polished example was covered with tape to provide a "polished only" surface as the reference, or control, surface. The exposed cured surface was brushed with a ORAL B™ 35 Soft Straight toothbrush (Oral B Laboratories, Belmont, Calif.) under a load of 5N of force at a frequency of 150 cycles/min (2.5 hz). The cured surface and toothbrush were immersed in a slurry of 50/50 by weight CREST™ Regular Flavor (Proctor & Gamble, Cincinnati, Ohio) toothpaste/distilled water during the brushing process. Toothbrushing on each sample was stopped after a 5000 stroke cycle. After toothbrushing, the "polished and brushed" surface was rinsed with water and the tape was removed. The rectangular sample was dried.

The roughness measurements for each "polished only" and "polished and brushed" example were obtained using a WYKO RST PLUS Surface Profiling System (WYKO Corporation, Tuscon, Ariz.). A 50×/0.55 NA objective and 0.5 transfer lens were used to image the samples. The data was collected in accordance with WYKO RST PLUS Operators Manual, using the VSI or Vertical Scanning Interferometry mode with the following instrumental conditions: Modulation threshold 1%, 0.636 microns per pixel, 368×238 pixels, and a standard scan speed.

Roughness, Ra, (DIN and ISO 4287 standard Ra) was calculated according to the procedures described in "Perthometer, Surface Texture Parameters" (Mahr GMBH, Gottingen, Germany ed. Sep. 01, 1999) using the software Vision™ (WYKO Corp., Tuson, Ariz.). The "cylinder" and "tilt" correction were selected in the software. The Ra number was calculated from an "area" or image, which was 174 μm×234 μm. An average Ra based on five areas for "polished and brushed" areas, and for "polished only" areas, on each example was collected. Overall average Ra for a "polished only" area of an example was not greater than 25 nm.

Crystallinity Index Procedure—in Reference to U.S. patent application Ser. No. 09/428,830, Filed on Oct. 28, 1999

This test was used to determine the presence of amorphous phase in a preferred cluster of non-heavy metal and metal oxide particles. Particle size of the phase standard (zirconium oxide, calcium stabilized Z-1083 Lot Number 173077-A-1, CERAC Inc, Milwaukee, Wis.) was reduced by ball milling and/or hand grinding using a boron carbide mortar and pestle to pass 325 mesh sieve. Individual mixtures were prepared consisting of 0.400 grams of sample and 0.100 grams of mass standard, a material incorporated into samples being evaluated for crystallinity index to normalize X-ray intensity values based on amount of material present in a sample. Tungsten metal powder (<3 μm) was the mass standard used. Mixtures of the samples were blended under ethanol using an agate mortar and pestle and allowed to dry under flowing nitrogen. A similar mixture composed of the phase standard was also prepared to serve as the crystallinity index reference. The dried mixtures were removed from the mortar and pestle by spatula and fine brush and subsequently transferred to individual sample containers. Portions of each sample were prepared as ethanol slurries on sample holders containing flush mounted glass inserts. Multiple X-ray diffraction scans were obtained from each sample and phase standard mixture by use of a vertical Bragg-Bretano diffractometer (constructed by Philips Electronic Instuments, Mahwah, N.J.) employing copper $K_\alpha$ radiation, variable incident slit, fixed exit slit, graphite diffracted beam monochromator, and proportional counter registry of the scattered radiation. Scans were conducted from 25–55 degree (2θ) employing a 0.04 degree step size. A 4 second dwell time was used for standard mixture while a 20 second dwell time was employed for sample mixtures to improve counting statistics. A minimum of 10 scans should be taken. The X-ray generator (Spellman High Voltage Electronics Corporation, Hauppage, N.Y.) was operated at a setting of 40 kV and 20 mA. Peak areas for the observed diffraction maxima due to zirconia and tungsten phases were measured by profile fitting observed diffraction peaks within the 25–55 degree (2θ) scattering angle range. The following peak areas were evaluated depending on the zirconia phase found to be present:

| | |
|---|---|
| cubic | (1 1 1), (2 0 0), and (2 2 0) |
| tetragonal | (1 0 1), (0 0 2)/(1 1 0), and (1 1 2)/(2 0 0) |
| monoclinic | (−1 1 1), (1 1 1), (0 0 2), (0 2 0), and (2 0 0) |

The X-ray scattering of internal mass standard was evaluated by measurement of cubic tungsten (1 1 0) peak area. A Pearson VII peak shape model and linear background model were employed in all cases. The profile fitting was accomplished by use of the capabilities of the JADE (version 3.1, Materials Data Inc. Livermore, Calif.) diffraction software suite. The peak areas of zirconia peaks outlined above were summed to produce a total zirconia scattered intensity value [(Zirconia Area)$_{sample}$] for each sample as well as standard [(Zirconia Area)$_{standard}$]. These total zirconia scattered intensity values were divided by respective cubic tungsten (1 1 0) peak areas to produce the ratio [$R_{sample}$] for each sample as well as the phase standard [$R_{standard}$]. The arithmetic mean of $R_{sample}$ and $R_{standard}$ are calculated using individual values obtained from the multiple runs of sample and standard, repectively. The crystallinity index [$X_c$] for each sample was calculated as the ratio of $R_{sample(mean)}$ to $R_{standard(mean)}$.

$R_{sample(i)}$=[(Total Zirconia Area)$_{sample}$]/[(Tungsten Area)$_{sample}$]

$R_{standard(i)}$=[(Total Zirconia Area)$_{standard}$]/[(Tungsten Area)$_{standard}$]

$R_{sample(mean)}$=[$\Sigma R_{sample(i)}$]/$N_{sample}$ where $N_{sample}$=number of sample scans $R_{standard(mean)}$=[$\Sigma R_{standard(i)}$]/$N_{standard}$ where $N_{standard}$=number standard scans $X_c = R_{sample(mean)}/R_{standard(mean)}$ Crystallite Particle Size and Crystal Form Content Particle size of dried zirconia sample from U.S. patent application Ser. No. 09/428,374, filed on Oct. 28, 1999, was reduced by hand grinding using an agate mortar and pestle. A liberal amount of the sample was applied by spatula to a glass microscope slide on which a section of double coated tape had been adhered and pressed into the adhesive on the tape by forcing the sample against the tape with spatula blade. Excess sample was removed by scraping the sample area with the edge of the spatula blade, leaving a thin layer of particles adhered to the adhesive. Loosely adhered materials remaining after the scraping were remove by forcefully tapping the microscope slide against a hard surface. In a similar manner, corundum (Linder 1.0 μm alumina polishing powder, Lot Number C062, Union Carbide, Indianapolis, Ind.) was prepared and used to calibrate diffractometer for instrumental broadening.

X-ray diffraction scans were obtained from by use of a diffractometer employing copper $K_\alpha$ radiation and Inel CPS120 (Inel Inc, Stratham, N.H.) position sensitive detector registry of the scattered radiation. The detector has a nominal angular resolution of 0.03 degrees (2θ) and received scattering data from 0 to 115 degree (2θ). The X-ray generator was operated at a setting of 40 kV and 10 mA and fixed incident beam slits were used. Data was collected for 60 minutes at a fixed take-off (incident) angle of 6 degrees. Data collections for the corundum standard were conducted on three separate areas of several individual corundum mounts. Data was collected on three separate areas of the thin layer sample mount.

Observed diffraction peaks were identified by comparison to the reference diffraction patterns contained within the ICDD powder diffraction database (sets 1–47, International Center for Diffraction Data, Newton Square, Pa.) and attributed to either cubic/tetragonal (C/T) or monoclinic (M) forms of zirconia. The amounts of each zirconia form were evaluated on a relative basis and the form of zirconia having the most intense diffraction peak was assigned the relative intensity value of 100. The strongest line of each of the remaining crystalline zirconia forms were scaled relative to the most intense line and given a value between 1 and 100.

Peak widths for the observed diffraction maxima due to corundum were measured by profile fitting. The relationship between mean corundum peak widths and corundum peak position (2θ) was determined by fitting a polynomial to these data to produce a continuous function used to evaluate the instrumental breadth at any peak position within the corundum testing range. Peak widths for the observed diffraction maxima due to zirconia were measured by profile fitting observed diffraction peaks. The following peak widths were evaluated depending on the zirconia phase found to be present:

cubic/tetragonal (C/T): (1 1 1)

monoclinic (M): (−1 1 1), and (1 1 1)

Peak widths were found as the peak full width at half maximum (FWHM) having units of degrees using a Pearson VII peak shape model, with $K_{\alpha 1}$ and $K_{\alpha 2}$ wavelength components accounted for, and linear background model. The profile fitting was accomplished by use of the capabilities of the JADE (version 3.1, Materials Data Inc., Livermore, Calif.) diffraction software suite. Sample peak widths were evaluated for the three separate data collections obtained for the same thin layer sample mount.

Sample peaks were corrected for instrumental broadening by interpolation of instrumental breadth values from corundum instrument calibration and corrected peak widths converted to units of radians. Corrected sample peak width ($\beta$) were used to evaluate primary crystal (crystallite) size by application of the Scherrer equation. The arithmetic mean of the cubic/tetragonal (C/T) and monoclininc phases (M) were calculated.

$\beta$=[calculated peak FWHM−instrumental breadth] (converted to radians)

Crystallite Size $(D)=K\lambda/\beta(\cos\theta)$ where:

K=form factor (here 0.9);

$\lambda$=wavelength (1.540598 Å);

$\beta$=calculated peak width after correction for instrumental broadening (in radians); and $\theta$=½ the peak position (scattering angle).

Cubic/Tetragonal Mean Crystallite Size=$[D(1\ 1\ 1)_{area1}+D(1\ 1\ 1)_{area2}+D(1\ 1\ 1)_{area3}]/3$ Monoclinic Mean Crystallite Size=$[D(-1\ 1\ 1)_{area1}+D(-1\ 1\ 1)_{area2}+D(-1\ 1\ 1)_{area3}+D(1\ 1\ 1)_{area1}+D(1\ 1\ 1)_{area2}+D(1\ 1\ 1)_{area3}]/6$ The crystallite size is reported in the format:

[$C/T$ crystallite size](parts $C/T$)+[$M$ crystallite size](parts $M$)

Weighted average=[(% $C/T$)($C/T$ size)+(% $M$)($M$ size)]/100 where:

% C/T=the percent crystallinity contributed by the cubic and tetragonal crystallite content of the $ZrO_2$ sol;

C/T size=the size of the cubic and tetragonal crystallites;

% M=the percent crystallinity contributed by the monoclinic crystallite content of the $ZrO_2$ sol; and M size=the size of the monoclinic crystallites.

Crystallinity Index—in Reference to U.S. patent Ser. No. 09/428,374, Filed on Oct. 28, 1999

Particle size of the phase standard (zirconium oxide, calcium stabilized Z-1083 Lot Number 173077-A-1, CERAC Inc, Milwaukee, Wis.) was reduced by ball milling and/or hand grinding using a boron carbide mortar and pestle to pass 325 mesh sieve. Individual mixtures were prepared consisting of 0.400 grams of sample and 0.100 grams of mass standard, a material incorporated into samples being evaluated for crystallinity index to normalize X-ray intensity values based on amount of material present in a sample. Tungsten metal powder (<3 $\mu$m) was the mass standard used. Mixtures of the samples were blended under ethanol using an agate mortar and pestle and allowed to dry under flowing nitrogen. A similar mixture composed of the phase standard was also prepared to serve as the crystallinity index reference. The dried mixtures were removed from the mortar and pestle by spatula and fine brush and subsequently transferred to individual sample containers. Portions of each sample were prepared as ethanol slurries on sample holders containing flush mounted glass inserts. Multiple X-ray diffraction scans (a minimum or 10 scans for both sample and standard) were obtained from each sample and phase standard mixture by use of a vertical Bragg-Bretano diffractometer (constructed by Philips Electronic Instruments, Mahwah, N.J.) employing copper $K_\alpha$ radiation, variable incident slit, fixed exit slit, graphite diffracted beam monochromator, and proportional counter registry of the scattered radiation. Scans were conducted from 25–55 degree (2$\theta$) employing a 0.04 degree step size. A 8 second dwell time was used for standard mixture while a 20 second dwell time was employed for sample mixtures to improve counting statistics. The X-ray generator (Spellman High Voltage Electronics Corporation, Hauppage, N.Y.) was operated at a setting of 40 kV and 20 mA. Peak areas for the observed diffraction maxima due to zirconia and tungsten phases were measured by profile fitting observed diffraction peaks within the 25–55 degree (2$\theta$) scattering angle range. The following peak areas were evaluated depending on the zirconia phase found to be present:

| | |
|---|---|
| cubic (C) | (1 1 1), (2 0 0), and (2 2 0) |
| tetragonal (T) | (1 0 1), (0 0 2)/(1 1 0), and (1 1 2)/(2 0 0) |
| monoclinic (M) | (−1 1 1), (1 1 1), (0 0 2), (0 2 0), and (2 0 0) |

The X-ray scattering of internal mass standard was evaluated by measurement of cubic tungsten (1 1 0) peak area. A Pearson VII peak shape model and linear background model were employed in all cases. The profile fitting was accomplished by use of the capabilities of the JADE (version 3.1, Materials Data Inc. Livermore, Calif.) diffraction software suite. The peak areas of zirconia peaks outlined above were summed to produce a total zirconia scattered intensity value [(Zirconia Area)$_{sample}$] for each sample as well as standard [(Zirconia Area)$_{standard}$]. These total zirconia scattered intensity values were divided by respective cubic tungsten (1 1 0) peak areas to produce the ratio [$R_{sample}$] for each sample as well as the phase standard [$R_{standard}$]. The arithmetic mean of $R_{sample}$ and $R_{standard}$ are calculated using individual values obtained from the multiple runs of sample and standard, respectively. The crystallinity index [$X_c$] for each sample was calculated as the ratio of $R_{sample(mean)}$ to $R_{standard(mean)}$.

$R_{sample(i)}$=[(Total Zirconia Area)$_{sample}$]/[(Tungsten Area)$_{sample}$]

$R_{standard(i)}$=[(Total Zirconia Area)$_{standard}$]/[(Tungsten Area)$_{standard}$]

$R_{sample(mean)}$=[$\Sigma R_{sample(i)}$]/$N_{sample}$ where $N_{sample}$=number of sample scans $R_{standard(mean)}$[$\Sigma R_{standard(i)}$]/$N_{standard}$ where $N_{standard}$=number standard scans $X_c$=$R_{sample(mean)}$/$R_{standard(mean)}$ Photon Correlation Spectroscopy This test was used to determine the particles size of suitable heavy metal oxides in a sol. The weight average mean particle diameter of the zirconia particles was determined by Photon Correlation Spectroscopy using a Coulter N4 Submicron Particle Sizer (available from Coulter Corporation, Miami Fla.). Dilute zirconia sol samples were filtered through a 0.45 μm filter using syringe-applied pressure into a glass cuvette. The remaining volume of the cuvette was filled with water, covered, and repeatedly inverted to remove air bubbles. The cuvette was wiped down to remove fingerprints and dust prior to taking any measurements. Light scattering intensity was measured to ensure that an appropriate concentration of sol was sampled. If the intensity was too high, a portion of the cuvette's contents was removed and the remaining contents diluted with water. If the intensity was too low, several more drops of filtered sol were added to the sample and the solution mixed by repeatedly inverting the cuvette. Prior to starting data acquisition the temperature of the sample chamber was allowed to equilibrate for 5 minutes at 25° C. Th supplied software was used to do a SDP analysis (1.0 nm–1000 nm) with an angle of 90°. The analysis was performed using 25 data bins. The following values were used in the calculations: refractive index of water=1.333, viscosity of water 0.890 cP, and refractive index for zirconia particles=1.9. Data acquisition immediately ensued for a period of 3:20 minutes. The reported PCS number is the mean diameter based on weight analysis that results from this procedure.

| Name | Description | Supplier |
|---|---|---|
| \multicolumn{3}{c}{ABBREVIATIONS/DEFINITIONS} | | |
| BISEMA6 | ethoxylated (6 mole ethylene oxide)bisphenol A dimethacrylate | Sartomer CD541, Sartomer (Exton, PA) |
| UDMA | Diurethane dimethacrylate, CAS No. 41137-60-4, which is commercially available as Rohamere 6661-0 | Rohm Tech, Inc. (Malden, MA) |
| BisGMA | 2,2-bis[4-(2-hydroxy-3-methacryloyloxy-propoxy)phenyl]propane | |
| TEGDMA | Triethyleneglycol dimethacrylate | |
| CPQ | Camphorquinone | |
| DPI PF6 | Diphenyl Iodonium Hexafluorophosphate | |
| EDMAB | Ethyl 4-dimethylaminobenzoate | |
| BHT | 2,6-Di-tert-butyl-4-methylphenol | |
| Norbloc 7966 | (CAS 96478-09-0) 2-(2'-Hydroxy-5'-methacryloxyethylphenyl)-H-benzotriazole | Janssen Pharmaceutica (Titusville, PA) |
| Tinuvin-P | 2-(2H-Benzotriazol-2-yl)-4-methylphenol | Ciba Specialty Chemicals Inc. (Basel, Switzerland) |
| TFAA | Trifluoroacetic acid | |
| MEEAA | 2-[2-(2-methoxy)ethoxy]ethoxy acetic acid | |
| MA | Methacryiic Acid | |
| AA | Acrylic Acid | |
| AAEM | 2-(acetoacetoxy)ethyl methacrylate | Eastman Chemical (Kingsport TN) |
| 1-vinyl imidazole | | |
| 2-(Dimethylamine) ethyl methacrylate | | |
| A174 | gammamethacryloxypropyltrimethoxysilane | Witco Osi Specialties (Danbury, CT) |
| A1230 | Propietary nonionic Silane | Witco Osi Specialties (Danbuty, CT) |
| Nalco 2327 | is an ammonium hydroxide stabilized colloidal silica sol with a pH of about 9.3 with nominal particle diameter of 20 nm. Solids content is about 40%. | Nalco (Naperville, IL) |
| Nalco 2329 | is a sodium hydroxide stabilized colloidal silica sol with a pH of about 8–9 and a nominal particle diameter of 7.5 nm. Solids content is about 40%. | Nalco (Naperville, IL) |
| Nyacol Zr (acetate) | is an aqueous acetate stabilized $ZrO_2$ sol with 5–10 nm average primary particle size. | PQ Corp. (Ashland, MA.) |
| Nyacol Zr 20/10 | which is an aqueous ZrO2 sol of 20 wt % with 5–10 nm ZrO2 particles. | PQ Corp. (Ashland, MA.) |
| Nyacol SN15-CG | is an aqueous 15 wt % of colloidal SnO2 10–15 nm particles with an ammonium counter ion. | PQ Corp (Ashland, MA) |
| Silux Plus | Silux Plus ™ Anterior Restorative, 3M ™ | 3M Co. (St. Paul, MN) |
| Z100 | Z100 ™ Restorative, 3M υ | 3M Co. (St. Paul, MN) |
| Methoxypropanol | Methoxy-2-propanol | |
| Scotchbond | Scotchbond ™ Multi-Purpose Dental Adhesive System, 3M ™ | 3M Co. (St. Paul, MN) |
| Zirconia Sol I | U.S. Pat. No. 5,037,579 an aqueous sol with 33% $ZrO_2$ | |
| Zirconia Sol II | cubic or tetragonal Zr | |

| Constituent | PBW |
|---|---|
| Resin A | |
| BisGMA | 48.70 |
| TEGDMA | 48.69 |
| EDMAB | 1.00 |
| CPQ | 0.17 |
| Tinuvin-P | 1.00 |
| DPIHFP | 0.6 |
| Resin B | |
| BisGMA | 48.58 |
| TEGDMA | 49.57 |

-continued

| Constituent | PBW |
|---|---|
| EDMAB | 0.6 |
| CPQ | 0.25 |
| Tinuvin-p | 0.98 |
| Resin C | |
| bisGMA | 24.18 |
| UDMA | 33.85 |
| bisEMA6 | 33.85 |
| TEGDMA | 4.84 |
| CPQ | 0.2 |
| DPIHFP | 0.5 |
| EDMAB | 1.0 |
| BHT | 0.1 |
| Norbloc 7966 | 1.5 |

Preparatory Examples

Preparatory Example 1

2-hydroxymethyl-2-[(N-methacryloxyethyl) carbamoylmethyl]propionic acid (PAMA)Synthesis The reactor was first charged with an excess amount of 2,2-bis(hydroxymethyl)propionic acid (BHMPA) (139.94 g, 1.043 mole), 2,6-Di-tert-butyl-4-methylphenol (0.2322 g, 1.054 mmole), triphenyl antimony (0.1891 g, 0.536 mmole), and dibutlytin dilaurate (0.6801 g, 1.077 mmole). The starting material, BHMPA, was only slightly soluble in THF at room temperature. Isocyanatoethylemethacrylate (IEM) was gradually dripped (80.94 g, 0.522 mole) into the above mixture. The reaction was run at 60° C. for 24 hours while stirring constantly. At the end of the reaction, most of the unreacted BHMPA settled out as white solid powder after the solution was cooled down. Unreacted BHMPA was filtered off by vacuum filtration, and the solvent was then stripped off. The recovered BHMPA could be used in future reactions.

After the removal of the solvent, the product became slightly cloudy due to slow precipitation of residual BHMPA. Enough diethyl ether was added to dissolve the product and then the solution was allowed to sit overnight (approximately 18 hours) undisturbed to precipitate out most of the remaining BHMPA in solution. The white precipitate was filtered off by vacuum filtration, and diethyl ether was stripped off. The resulting product, 2-hydroxymethyl-2-[(N-methacryloxyethyl)carbamoylmethyl]propionic acid (PAMA) was a colorless, flowable liquid. The purity of PAMA in the final product was approximately 80% by molar ratio, with 2,2-di(N-methacryloxyethyl carbamoylmethyl) propionic acid (PDMA) being the main side-product (approximately 17%) and small amounts of remaining BHMPA (approximately 3%).

Preparatory Example 2

Mono(methacryloxypolyethyleneglycol)succinate Synthesis

Polyethyleneglycol methacrylate (16.00 g) and succinic anhydride (4.15 g) were charged to a 1 L beaker and heated to 80 C. with shaking. The reaction was stopped after 24 hr and a clear somewhat viscous liquid was obtained. IR spectroscopy confirmed reaction of the anhydride. The compound was named mono(methacryloxypolyethyleneglycol) succinate. The structure was determined to be

$CH_2=C(CH_3)C(O)OCH_2CH_2[OCH_2CH_2]_nOC(O)CH_2CH_2CO_2H$ where n=6–8.

Filler A

Treated Fumed Silica OX-50 (DeGussa) was made as follows: a solution of 3312 g MeOH and 720 g deionized water was premixed for 1 minute. Glacial Acetic Acid, 1024 g, was slowly added to the water followed by 4968 g A-174 silane. The above solution was mixed for 1 hour. At the end of the hydrolysis step, the solution was clear. The solution was used within 30 minutes after hydrolysis. The above solution and 20700 g OX-50 powder were blended for approximately 40 minutes and the treated filler was immediately discharged into drying trays, and was dried at 67 C. for 3.75 hours and then another 1.25 hours at 100 C. The dried filler was screened through a 74 Mm nylon screen in a vibratory screener (Vortisiv V/S 10010, Salem, Ohio).

Filler B

Filler B was prepared by mixing together a 14.95 g MEEAA to 210 g of Zirconia Sol of U.S. Pat. No. 5,037,579. Thorough mixing for two minutes yielded a homogenous mixture. A solution of 24.36 g of Preparatory Example 1 in 25 g of ethanol was then added to the beaker. The contents were mixed thoroughly using a magnetic stir bar for 60 minutes followed by spray-drying using a Buchi spray drier (Buchi/Brinkmann Mini Spray Dryer Model 190, Brinkmann Instruments, Inc. Westbury, N.Y.) at 200° C. inlet temperature and 85–100° C. outlet temperature.

Filler C

Filler C was prepared by mixing together a 250 g portion Nyacol Zr(acetate), 25.8 g methacrylic acid and 53.4 g MEEAA. The sol was thoroughly mixed for approximately 1 hour to yield a homogenous mixture. The resultant mixture was spray-dried using a Buchi spray drier at 200° C. inlet temperature and 85–100° C. outlet temperature.

Filler D

Filler D was prepared from of Nyacol Zr 20/10 which is an aqueous ZrO2 sol of 20 wt % of 5–10 nm ZrO2 particles. The solution was spray-dried using a Buchi spray drier at 200° C. inlet temperature and 85–100° C. outlet temperature.

Filler E

Filler E was prepared by mixing a 7 portion of OX50 and an 80 g portion of water, to a 20 g of the Nyacol SN15-CG. The pH of the mixture was adjusted to 3.3 with TFAA. Two grams of A174 were then added to the mixture. After mixing for 60 minutes using a magnetic stir bar, the solution was spray-dried using a Buchi spray drier at 200° C. inlet temperature and 85–100° C. outlet temperature.

Filler F

Filler F was prepared by thoroughly mixing 250 g Nalco 2329, 281.0 g methoxy-2-propanol and 3.72 g of A174. The Nalco 2329 was weighed into a 2 L beaker. The alcohol and silane were weighed into a 1 L beaker and mixed together. The alcohol solution was added to the silica sol slowly with swirling (1–2 min). The resultant mixture was reacted at 80 C. for 16 hr to produce a modified silica sol. A 1 kg of water was added to the modified silica sol. This mixture was spray-dried using a Buchi spray drier at 200° C. inlet temperature and 85–100° C. outlet temperature.

EXAMPLE 1

Materials A–E were made by thoroughly mixing the constituents listed in Table 1. The materials were hardened and their mechanical and optical properties evaluated according to the Radiopacity, Visual Opacity (VO), Compressive Strength (CS) and Diametral Tensile Strength (DTS) methods previously described.

TABLE 1

Final Composition of Materials.

| Materials A–E | Resin C (pbw) | Filler B (pbw) | Filler A (pbw) |
|---|---|---|---|
| 1A | 40.00 | 13.75 | 46.25 |
| 1B | 40.00 | 18.00 | 42.00 |
| 1C | 40.00 | 22.25 | 37.75 |
| 1D | 49.48 | 15.16 | 35.36 |
| 1E | 30.52 | 20.84 | 48.64 |

The properties of the hardened materials of examples 1–5 were measured and reported in Table 2 along with the properties of Silux Plus, a commercial product.

TABLE 2

Properties of Materials of Example 1

| Examples | DTS (MPa) | CS (MPa) | Visual opacity | Radiopacity |
|---|---|---|---|---|
| Comparative Silux Plus | 49.52 | 358.12 | 0.35 | 0.26 |
| 1A | 67.46 | 417.19 | 0.37 | 0.77 |
| 1B | 63.41 | 444.42 | 0.40 | 0.89 |
| 1C | 57.87 | 413.28 | 0.40 | 1.00 |
| 1D | 62.10 | 430.48 | 0.42 | 0.78 |
| 1E | 58.11 | 422.54 | 0.39 | 1.13 |

The compressive and diametral tensile strengths of the hardened nanomer materials were higher than that of Silux Plus. Unlike Silux Plus, the examples exhibited radiopacity. Visual opacity (VO) values were quite acceptable for dental restoratives.

EXAMPLE 2

A material was prepared by thorougly mixing together 25 pbw Resin C, 25 pbw of Filler C, and 50 pbw of Filler A. The material was hardened and its mechanical and optical properties were evaluated according to the Radiopacity and Diametral Tensile Strength (DTS) methods previously described. The radiopacity of the dental material was 1.0 compared to 0.26 for commercial Silux Plus. The diametral tensile strength of example 6 (49.32 MPa) was not compromised (Silux Plus 49.52 MPa).

EXAMPLE 3

A material was prepared by thoroughly mixing 33.3 pbw of Resin C, 23.3 pbw treated of Filler B, 43.3 pbw Filler A. The material was hardened and the mechanical and optical properties evaluated according to the Radiopacity, Visual Opacity (VO), Compressive Strength (CS) and Diametral Tensile Strength (DTS) methods previously described.

TABLE 3

| Property | Example 3 | Silux Plus |
|---|---|---|
| DTS (MPa) | 63.60 | 49.52 |
| CS (MPa) | 407.88 | 358.12 |
| Radiopacity | 1.15 | 0.26 |
| Visual Opacity | 0.39 | 0.35 |

The first three properties, DTS, CS and radiopacity, were improved by the addition of the nanosized zirconia particles without compromising Visual Opacity as compared to Silux Plus.

EXAMPLE 4

To demonstrate the radiopacifying effect of nano-sized zirconia on dental composite, various amounts of Filler D, which was 61.2% ZrO2 after spray drying, were added into Resin A on a weight percent basis. The materials 4A–4I were hardened and their radiopaque properties were evaluated according to the methods previously described.

As seen in Table 4, without ZrO2, the resin exhibited a radiopacity of 0.108 mm Al; with 75% Filler D, the composite produced radiopacity of 4.5 mm Al.

TABLE 4

| Example 4 | Wt % of Filler D | Wt % of Resin A | Radiopacity (mm Al) |
|---|---|---|---|
| 4A | 0 | 100 | 0.108 |
| 4B | 10 | 90 | 0.217 |
| 4C | 20 | 80 | 0.5 |
| 4D | 30 | 70 | 0.766 |
| 4E | 40 | 60 | 1.166 |
| 4F | 50 | 50 | 2 |
| 4G | 60 | 40 | 2.5 |
| 4H | 70 | 30 | 4 |
| 4I | 75 | 25 | 4.5 |

EXAMPLE 5

7.5 grams of filler made in Filler E were thoroughly mixed into 2.5 grams of Resin B. The resultant material was very translucent. The material was hardened according to the DTS procedure previously described, and the dental composite became more opaque and turned light blue. The blue color faded from the hardened material after a few days.

EXAMPLE 6

A modified silica sol was prepared by adding 400.1 g Nalco 2329 (160 g SiO2 by weight), 449.9 g methoxy-2-propanol, 4.72 g A174, and 1.18 g A1230. The Nalco 2329 was weighed into a 2 L beaker. The alcohol and two silanes were weighed into a 1 L beaker and mixed together. The alcohol solution was added to the silica sol slowly with swirling (1–2 min). The mixture was reacted at 80 C. for 16 hr to produce a modified silica sol.

An organosol was prepared from 8.34 g Resin B and 64.7 g modified silica sol (12.45 g of modified SiO2 by weight) and mixed in a 200 ml round bottom flask. The alcohol and water were removed via rotary evaporation and the organosol was sampled periodically. The distillation of the organosol was stopped when the composition of the organosol as analyzed by gas chromatography had the following composition:

52.2% Modified Silica
35.0% Resin B
12.8% Alcohol

A 1.25 g portion of Filler B was added to a 5 g portion of the above organosol. Filler B dispersed into the organosol without any sign of separation or inhomogeneity. This material was placed in an oven at 85–90° C. for up to four hours to remove the alcohol. The resultant material was a material with the following composition:

47.20% Modified Silica
22.20% Filler B
30.60% Resin B

The material was hardened and its mechanical and optical properties evaluated according to the Radiopacity, Visual Opacity (VO), Compressive Strength (CS) and Diametral Tensile Strength (DTS) methods previously described. The mechanical and optical properties of example 6 are given in Table 5 and compared to Silux Plus.

TABLE 5

| Property | Example 6 | Silux Plus |
|---|---|---|
| DTS (MPa) | 69.83 | 49.52 |
| CS( MPa) | 383.45 | 358.12 |
| Radiopacity | 1.15 | 0.26 |
| Visual Opacity | 0.26 | 0.35 |

EXAMPLE 7

To make the fillers for examples 7A–7D, various amounts of A174, as listed in Table 9, were added to a mixture of 250 g of the Nalco 2329 sol and 281 g methoxypropanol. The Nalco 2329 was weighed into a 2 L beaker. The alcohol and silane were weighed into a 1 L beaker and mixed together. The alcohol solution was added to the silica sol slowly with swirling (1–2 min). The four silane-treated silica sols were solvent-exchanged by mixing each silane-treated silica sol with 69 g of Resin B and heating the modified organic sol in an oven at 85–90 C. for 4 hours.

Filler B was thoroughly mixed with each of the four modified organic sols to make materials with final compositions of 31.5 pbw Resin B, 45.5 pbw of silane-treated silica and 23 pbw Filler B. The four materials were hardened according to the Visual Opacity and DTS methods previously described. The Visual Opacity and the DTS data are illustrated in Table 6.

TABLE 6

| | Example | | | |
|---|---|---|---|---|
| | 7A | 7B | 7C | 7D |
| Weight (g) of A174 Silane per 100 g SiO$_2$ | 1.86 | 3.72 | 7.44 | 11.16 |
| Visual opacity | 0.30 | 0.26 | 0.24 | 0.24 |
| DTS (Mpa) | 63.86 | 67.59 | 65.79 | 62.14 |

The treated silica with 3.72% of silane based on weight of silica produced the dental composite with the highest strength.

EXAMPLE 8

A 3 g portion of Zirconia sol I, 3 g of methoxypropanol, 2.2 mmol/g modifying agent as listed below in Tables 7a, 7b and 7c, and 1 gram of Resin as listed below in table 7a, 7b, and 7c were mixed and dried in an oven at 85° C. for 1.5 hours. After oven drying, the materials were hardened according to the Visual Opacity method previously described.

TABLE 7a

| Example # | 2.2 mmol modifying agent per gram ZrO$_2$ | Visual Opacity in Resin C |
|---|---|---|
| 8A | MEEAA | 0.13 |
| 8B | Acid made in Preparatory Example 1 | 0.33 |
| 8C | AAEM | 0.34 |
| 8D | 1-vinyl imidazole | 0.42 |
| 8E | 2-(Dimethylamine) ethyl methacrylate | 0.41 |
| Comparative 8F | No Modifying Agent | 0.33 |

TABLE 7b

| Example # | 1.1 mmol/gram MEEAA and 1.1 mmol/gram listed modifying agent on ZrO$_2$ | Visual Opacity in Resin B |
|---|---|---|
| 8G | MEEAA | 0.10 |
| 8H | MA | 0.12 |
| 8I | Acid made in Preparatory Example 1 | 0.12 |
| 8J | AA | 0.16 |
| 8K | Acid made in Preparatory Example 2 | 0.17 |
| 8L | AAEM | 0.15 |
| 8M | 1-vinyl imidazole | 0.15 |
| 8N | 2-(Dimethylamine) ethyl methacrylate | 0.16 |
| Comparative 8O | No Modifying Agent | 0.13 |

TABLE 7c

| Example # | 1.1 mmol/gram MEEAA and 1.1 mmol/gram listed modifying agent on ZrO$_2$ | Visual Opacity in Resin C |
|---|---|---|
| 8P | MEEAA | 0.13 |
| 8Q | MA | 0.21 |
| 8R | Acid made in Preparatory Example 1 | 0.16 |
| 8S | AA | 0.21 |
| 8T | Acid made in Preparatory Exampte 2 | 0.15 |
| 8U | AAEM | 0.20 |
| 8V | 1-vinyl imidazole | 0.23 |
| 8W | 2-Dimethylamine) ethyl methacrylate | 0.25 |
| Comparative 8X | No modifying agent | 0.21 |

Basic modifying agents such as Examples 8D and 8E adversely affected Visual Opacity. With proper acid treatments, good dispersions are evidenced either by a decrease in Visual Opacity or no chance relative to comparative example 8O and 8F. Combination of MEEAA with most additives exhibited good dispersion as seen in Table 7B and 7C.

EXAMPLE 9

For the five materials 9A–9F, Filler B was used for example 9A. Materials 9B–9E were made using the procedure for making, filler B with the modification of substituting the acids as listed in Table 8. The five materials were thoroughly mixed to contain a final composition of 58% Filler F, 21% of acid modified Zirconia, and 21% of Resin C. The mechanical and optical properties of the five hardened materials were evaluated according to the Visual Opacity, Radiopacity and DTS methods previously described.

TABLE 8

| Materials | Acid loading on ZrO$_2$ | Visual Opacity | Radiopacity | DTS (Mpa) |
|---|---|---|---|---|
| 9A | 1.1 mmol/g MEEAA and 1.1 mmol/g Acid made in Preparatory Example 1 | 0.18 | 1.25 | 62.14 |
| 9B | 2 mmol/g Acid made in Preparatory Example 1 | 0.41 | 1.25 | 59.66 |
| 9C | 1.1 mmol/g MEEAA and 1.1 mmol/g Acrylic Acid | 0.21 | 1.55 | 61.38 |
| 9D | 0.6 mmol/g MEEAA and 1.6 mmol/g Acid made in Preparatory Example 1 | 0.27 | 1.20 | 56.97 |

TABLE 8-continued

| Materials | Acid loading on $ZrO_2$ | Visual Opacity | Radio-pacity | DTS (Mpa) |
|---|---|---|---|---|
| 9E | 0.95 mmol/g Acid made in Preparatory Example 2 and 1.15 mmol/g AA Acid | 0.36 | 1.06 | 68.76 |

EXAMPLE 10

The materials listed in Table 9 were thoroughly mixed with different filler types and filler loadings into Resin C. The four materials were hardened and their mechanical and optical properties evaluated according to the Radiopacity, Visual Opacity, Compressive Strength, and Diametral Tensile Strength methods previously described. The results were compared to Silux Plus.

TABLE 9

| Example Number | Wt % Resin C | Silica Source | Total filler % | Wt % Silica | Wt % Filler B | DTS (Mpa) | CS (MPa) | Visual opacity | Radiopacity |
|---|---|---|---|---|---|---|---|---|---|
| Comparative 10A Silux Plus | 33.3 | Filler A | 66.7 | 66.7 | 0.0 | 49.52 | 358.12 | 0.34 | 0.26 |
| 10B | 33.3 | Filler A | 66.7 | 31.7 | 35.0 | 63.60 | 407.88 | 0.39 | 1.15 |
| 10C | 31.0 | Filler F | 69.0 | 46 | 23 | 69.83 | 383.45 | 0.26 | 1.2 |
| 10D | 20.0 | Filler F | 80.0 | 53.33 | 26.67 | 69.66 | 382.28 | 0.22 | 1.6 |

EXAMPLE 11

Nyacol Zr (Ac) (200.04 g) and MEEAA (17.8 g, 2.5 mmole/g ZrO2) were charged to a liter beaker and the resulting mixture stirred at room temperature (approximately 22° C.) for 30 minutes. Water and excess acetic acid were removed and the mixed salt recovered as a dry solid (78.17 g) by allowing the reaction mixture to evaporate in an evaporating dish placed in a circulating air oven maintained at approximately 85° C. for approximately 18 hours. The polyetheracid zirconium salt was dissolved in deionized water (3047.4 g) to produce a clear polyetheracid zirconium salt solution (3125.6 g), which was poured into a 2 liter, unstirred, stainless steel Parr Reactor (Parr Instrument Co., Illinois), and the autoclave pressurized to about 2.75 bars (40 psi). The autoclave was subsequently heated to 100° C. in approximately 2 hr, to 150° C. over a period of approximately 1.5 hours, and finally to 175° C. (12 bars) and maintained at that temperature for 15 hours. The autoclave was cooled and depressurized over a period of 2–3 hr. The zirconia sol of the present invention was obtained as a clear liquid with an opalescent blue/white color with no sediment. Photon Correlation spectroscopy gave a weight average mean particle diameter of 19.2 nm.

The sol was concentrated to approximately 20 wt % ZrO2 by distillation of the water to obtain a clear stable sol. The sol was dialyzed against deionized water—5 dialysis treatments using 2 liters of deionized water were used (IR showed no free acid). The sol was then dialyzed against 5 g acetic acid in 2 liters of water for three days. IR analysis confirmed exchange of a majority of the MEEAA for acetic acid. The resultant sol was stable (11.72% ZrO2). Dialysis was performed using Spectra/Por membrane tubing (Molecular Weight Cut Off of 3500, available from Fisher Scientific (Pittsburgh, Pa.)).

EXAMPLE 12

All four materials contained about 60% of Filler F silane treated silica, about 18.5% acid treated zirconia prepared as described in example 11 and about 21.5% Resin C. The materials were hardened and their mechanical and optical properties evaluated according to the Radiopacity, Visual Opacity, Compressive Strength and Diametral Tensile Strength methods previously described.

TABLE 11

| Material # | Acid loading on $ZrO_2$ | Visual Opacity | Radio-pacity | DTS |
|---|---|---|---|---|
| 12A | 0.22 mmol/g Acid made in Preparatory Example 2 | 0.18 | 1.60 | 59.03 |
| 12B | 0.44 mmol/g Acid made in Preparatory Example 2 | 0.16 | 1.58 | 63.86 |
| 12C | 0.35 mmol/g Acid made in Preparatory Example 2 and 0.33 mmol/g Acrylic Acid | 0.16 | 1.56 | 65.66 |

TABLE 11-continued

| Material # | Acid loading on $ZrO_2$ | Visual Opacity | Radio-pacity | DTS |
|---|---|---|---|---|
| 12D | 0.35 mmol/g Acid made in Preparatory Example 2 and 0.66 mmol/g Acrylic Acid | 0.17 | 1.5 | 63.38 |

EXAMPLE 13

Surface Polish and Tooth Brush Resistance

Example 13 was made by mixing 20 pbw of Resin C and 26.67 pbw of Filler B and 53.33 pbw of Filler F. The sample was subjected to the Toothbrush Abrasion Resistance Test and then evaluated for surface roughness values using the procedure described above. Table 12 provides the results and compares them to those obtained for microfill-type materials Silux Plus™ and Z100™.

TABLE 12

| Example | Surface Roughness after polishing before toothbrushing (Ra Average for polished area of example) Average of 5 area readings ($\mu$m) | Surface Roughness after tooth brushing (Ra Average for polished and brushed area of example) Average of 5 area readings ($\mu$m) |
|---|---|---|
| Comparative Z100 | .0151 | .2680 |
| Comparative Silux Plus | .0185 | .0889 |
| Example 13 | .0172 | .0967 |

EXAMPLE 14

The two Scotchbond adhesives 14A–14B with the different fillers and filler loadings were thoroughly mixed to make the compositions as described in Table 13. Adhesive strength to dentin and enamel of the two adhesives was evaluated by the following procedure. Five bovine teeth per adhesive composition of similar age and appearance were partially embedded in circular acrylic discs. The exposed portion of each tooth was ground flat and parallel to the acrylic disc using Grade 120 silicon carbide paper-backed abrasive mounted on a lapidary wheel, in order to expose the dentin or enamel. During this and subsequent grinding and polishing steps, the teeth were continuously rinsed with water. Further grinding and polishing of the teeth was carried out by mounting Grade 600 silicon carbide paper-backed abrasive on the lapidary wheel.

The polished teeth were stored in distilled water, and used for testing within 2 hours after polishing. The polished teeth were removed from the water and blotted dry. Using a Scotchbond™ kit 7540S, Scotchbond™ etchant was painted onto each of the polished tooth surfaces with a brush, allowed to stand for 15 seconds, rinsed with distilled water and then blotted dry. A single drop of Scotchbond™ primer was painted onto each of the polished tooth surfaces with a brush and immediately blown dry with compressed air for 5 sec.

Adhesive materials 14A thru 14B were painted onto each of the tooth surfaces, and hardened using a 10-second irradiation with a Visilux 2™ dental curing light. Previously prepared molds made from a 2-mm thick TEFLON™ (E. I. DuPont de Nemours, Wilmington, Del.) sheet with a 4 mm diameter hole through the sheet were clamped to each prepared tooth so that the central axis of the hole in the mold was normal to the tooth surface. The hole in each mold was filled Z100 restorative and cured with a Visilux 2™ dental curing light using a 40-second irradiation.

The teeth and molds were stored in distilled water at 37° C. for approximately 24 hours. The molds were then carefully removed from the teeth, leaving a molded button of restorative attached to each tooth.

Adhesive strength was evaluated by mounting the acrylic disk in a holder clamped in the jaws of an Instron apparatus with the polished tooth surface oriented parallel to the direction of pull. A loop of orthodontic wire (0.44 mm diameter) was placed around the restorative button adjacent to the polished tooth surface. The ends of the orthodontic wire were clamped in, the pulling jaw of the Instron apparatus, thereby placing the bond in shear stress. The bond was stressed until it (or the dentin or button) failed, using a crosshead speed of 2 mm/min.

TABLE 13

| Example | Composition | Enamel Adhesion Strength (MPa) | STDev (MPa) | Dentin Adhesion Strength (Mpa) | STDev (MPa) |
|---|---|---|---|---|---|
| 14A | 50% Scotchbond/ 38% Filler F/ 12% Filler B | 27.9 | 4.3 | 18.5 | 3.4 |
| 14 B | 62% Scotchbond/ 38% Filler B | 25.0 | 4.4 | 20.2 | 6.4 |

What is claimed is:

1. A dental material comprising non-heavy metal oxide particles having an average diameter of less than about 300 nm, an acid modified heavy metal oxide, and a hardenable resin.

2. The dental material of claim 1 wherein the heavy metal oxide are particles having an average diameter of less than about 100 nm.

3. The dental material of claim 1 wherein said non-heavy metal oxide particles are aggregated and have an average total aggregate size of less than about 300 nm.

4. The dental material of claim 1, wherein said heavy metal oxide are aggregated particles and have an average total aggregate size of less than about 200 nm.

5. The dental material of claim 1 wherein said heavy metal oxide particles are selected from the group consisting of zirconium oxide, cerium oxide, tin oxide, yttrium oxide, strontium oxide, barium oxide, lanthanum oxide, zinc oxide, ytterbium oxide, bismuth oxide and mixtures thereof.

6. The dental material of claim 1 wherein said hardenable resin is selected from the group consisting of acrylates, methacrylates, epoxies, and mixtures thereof.

7. The dental material of claim 1 wherein said material is selected from the group consisting of restoratives, adhesives, mill blanks, prostheses, orthodontic devices, casting materials, and dental coatings.

8. The dental material of claim 1 wherein said material, after hardening and subjecting to a Toothbrush Abrasion Resistance Test, has a surface roughness of less than about 0.2 $\mu$m.

9. The dental material of claim 1 wherein said material, after hardening, has a Visual Opacity value of less than about 0.5.

10. The dental material of claim 1 wherein said material, after hardening, has a diametral tensile strength greater than about 15 MPa.

11. The dental material of claim 1 wherein said material, after hardening, has a compressive strength greater than about 35 MPa.

12. A dental material comprising silica particles having an average diameter of less than about 300 nm, an acid modified heavy metal oxide, and a hardenable resin.

13. The dental material of claim 12 wherein said silica particles have an average diameter of less than about 200 nm.

14. The dental material of claim 12 wherein said silica particles have an average diameter of less than about 100 nm.

15. The dental material of claim 12 wherein the heavy metal oxide are particles having an average diameter of less than about 100 nm.

16. The dental material of claim 12 wherein said heavy metal oxide are particles having an average diameter of less than about 70 nm.

17. The dental material of claim 12 wherein said heavy metal oxide particles have an average diameter of less than about 60 nm.

18. The dental material of claim 12 wherein said heavy metal oxide is present in an effective amount to impart radiopacity to said dental material.

19. The dental material of claim 12 wherein said silica particles are aggregated and have an average total aggregate size less than about 300 nm.

20. The dental material of claim 12, wherein said silica particles are aggregated and have an average total aggregate size less than about 200 nm.

21. The dental material of claim 12, wherein silica particles are aggregated and have an average total aggregate size less than about 100 nm.

22. The dental material of claim 12, wherein said heavy metal oxide are aggregated particles and have an average total aggregate size of less than about 200 nm.

23. The dental material of claim 12, wherein said heavy metal oxide are aggregated particles and have an average total aggregate size of less than about 90 nm.

24. The dental material of claim 12 wherein said heavy metal oxide is selected from the group consisting of zirconium oxide, cerium oxide, tin oxide, and combinations thereof.

25. The dental material of claim 12 wherein said heavy metal oxide is a cubic or tetragonal zirconium oxide.

26. The dental material of claim 12 wherein said hardenable resin is selected from the group consisting of acrylates, methacrylates, epoxies, and mixtures thereof.

27. The dental material of claim 12 wherein said silica particles are selected from the group consisting of fumed silica, colloidal silica, and combinations thereof.

28. The dental material of claim 12 wherein said heavy metal oxide is zirconium oxide, and said hardenable resin is an acrylate.

29. The dental material of claim 12 further comprising an initiator to harden said hardenable resin.

30. The dental material of claim 12 wherein said material is selected from the group consisting of restoratives, adhesives, mill blanks, prostheses, orthodontic devices, casting materials, and dental coatings.

31. The dental material of claim 12 wherein said material, after hardening, has a Visual Opacity value of less than about 0.5.

32. The dental material of claim 12 wherein said material, after hardening, has a Visual Opacity value of less than about 0.35.

33. The dental material of claim 12 wherein said material, after hardening, has a Visual Opacity value of less than about 0.25.

34. The dental material of claim 12 wherein said material, after hardening, has a diametral tensile strength greater than about 15 MPa.

35. The dental material of claim 12 wherein said material, after hardening, has a diametral tensile strength greater than about 40 MPa.

36. The dental material of claim 12 wherein said material, after hardening, has a diametral tensile strength greater than about 60 MPa.

37. The dental material of claim 12 wherein said material, after hardening, has a compressive strength greater than about 35 MPa.

38. The dental material of claim 12 wherein said material, after hardening, has a compressive strength greater than about 200 MPa.

39. The dental material of claim 12 wherein said material, after hardening, has a compressive strength greater than about 350 MPa.

40. The dental material of claim 12 wherein said material, upon hardening and subjecting to a Toothbrush Abrasion Resistance Test, has a surface roughness of less than about 0.2 µm.

41. The dental material of claim 12 wherein said material, upon hardening and subjecting to a Toothbrush Abrasion Resistance Test, has a surface roughness of less than about 0.15 µm.

42. A method of making a dental material comprising:
    a) admixing a surface modifier with silica particles having an average diameter of less than about 300 nm;
    b) admixing an acid surface modifier with heavy metal oxide particles having an average diameter less than about 100 nm; and
    c) admixing said surface modified silica particles and acid modified heavy metal oxide particles with a hardenable resin.

43. The method according, to claim 42 further comprising:
    d) hardening said resin.

44. A method of using the dental material of claim 1 comprising:
    a) placing said material near or on a tooth surface;
    b) changing the topography of said material; and
    c) hardening said material.

45. The method according to claim 44 further comprising:
    d) finishing the surface of said hardened material.

46. The method according to claim 44, wherein said hardened material has a surface roughness of less than about 0.2 µm after being subjected to a Toothbrush Abrasion Resistance Test.

47. The method according to claim 44, wherein said hardened material has a surface roughness of less than about 0.15 µm after being subjected to a Toothbrush Abrasion Resistance Test.

48. The method according to claim 44, wherein a) thru c) are performed sequentially.

49. A method of using the dental material of claim 12 comprising:
    a) placing said material near or on a tooth surface;
    b) changing the topography of said material; and
    c) hardening said material.

50. The method according to claim 49 further comprising:
    d) finishing the surface of said hardened material.

51. The method according to claim 49, wherein said hardened material has a surface roughness of less than about 0.2 µm after being subjected to a Toothbrush Abrasion Resistance Test.

52. The method according to claim 49, wherein said hardened material has a surface roughness of less than about 0.15 µm after being subjected to a Toothbrush Abrasion Resistance Test.

53. The method according to claim 49, wherein a) thru c) are performed sequentially.

54. A dental material comprising non-heavy metal oxide particles having an average diameter of less than about 100 nm, acid modified heavy metal oxide particles having an average diameter of less than about 100 nm, and a hardenable resin.

55. The material of claim 54 wherein the acid modified heavy metal oxide particles are surface treated particles.

56. A method of using a dental material comprising:
    placing the material near or on a tooth surface;
    changing the topography of the material; and
    hardening the material,
wherein the dental material comprises non-heavy metal oxide particles having an average diameter of less than about 300 nm; surface treated heavy metal oxide particles; and a hardenable resin; and wherein the surface treatment provides heavy metal oxide particles that are stabilized to provide for dispersion in the hardenable resin.

57. The method of claim 56 wherein the surface treated heavy metal oxide particles have an average diameter of less than about 100 nm.

58. A method of using a dental material comprising:
    placing the material near or on a tooth surface;
    changing the topography of the material; and
    hardening the material,
wherein the dental material comprises non-heavy metal oxide, heavy metal oxide, and a hardenable resin; the heavy metal of the heavy metal oxide has an atomic number greater than 30 but less than 72; and each of the non-heavy metal oxides and heavy metal oxides present are particles having an average diameter of less than about 100 nm.

* * * * *

UNITED STATES PATENT AND TRADEMARK OFFICE
CERTIFICATE OF CORRECTION

PATENT NO. : 6,387,981 B1
DATED : May 14, 2002
INVENTOR(S) : Zhang, Xiaodong

It is certified that error appears in the above-identified patent and that said Letters Patent is hereby corrected as shown below:

Title page,
Item [56], References Cited, OTHER PUBLICATIONS, "Burgard et al.", reference, delete "Nanopower" and insert in place thereof -- Manpower --; and "Watts et al.", reference, delete "Dential" and insert in place thereof -- Dental --.
U.S. PATENT DOCUMENTS, delete "5,037,597" and insert in place thereof -- 5,037,579 --.

Column 4,
Line 3, delete "finsh" and insert in place thereof -- finish --.

Column 13,
Line 20, delete "includes" following "acids".

Column 14,
Line 62, delete "of the" and insert in place thereof -- after --.

Column 26,
Line 30, delete "($72^6$-xylenes)" and insert in place thereof -- $N^6$-xylenes) --.

Column 27,
Line 66, delete "inventiont" and insert in place thereof -- invention --.

Column 29,
Line 41, delete "procedure" and insert in place thereof -- procedure --.

Column 33,
Line 18, delete "monoclininc" and insert in place thereof -- monoclinic --.

UNITED STATES PATENT AND TRADEMARK OFFICE
CERTIFICATE OF CORRECTION

PATENT NO.   : 6,387,981 B1
DATED        : May 14, 2002
INVENTOR(S)  : Zhang, Xiaodong It is certified that error appears in the above-identified patent and that said Letters Patent is hereby corrected as shown below:

Column 34,
Line 33, delete "lincar" and insert in place thereof -- linear --.

Column 36,
Abreviations/Definitions, Name A1230, delete "Danbuty" and insert in place thereof -- Danbury --.

Column 45,
Line 66, delete "hardenablc" and insert in place thereof -- hardenable --.

Signed and Sealed this

Tenth Day of August, 2004

JON W. DUDAS
*Acting Director of the United States Patent and Trademark Office*